(12) United States Patent
Heysiattalab et al.

(10) Patent No.: US 10,290,091 B1
(45) Date of Patent: May 14, 2019

(54) FILAMENT INSPECTION SYSTEM

(71) Applicant: Arevo, Inc., Santa Clara, CA (US)

(72) Inventors: Saeed Heysiattalab, Santa Clara, CA (US); Chandrashekar Mantha, Santa Clara, CA (US); Mohammad Dadkhah Tehrani, San Jose, CA (US); Michael Peter Thompson, San Carlos, CA (US)

(73) Assignee: Arevo, Inc., Santa Clara, CA (US)

( * ) Notice: Subject to any disclaimer, the term of this patent is extended or adjusted under 35 U.S.C. 154(b) by 0 days.

(21) Appl. No.: 16/029,043

(22) Filed: Jul. 6, 2018

(51) Int. Cl.
*G06T 7/00* (2017.01)
*G01N 27/22* (2006.01)
*G01B 11/24* (2006.01)

(52) U.S. Cl.
CPC ............ *G06T 7/0004* (2013.01); *G01N 27/22* (2013.01); *G06T 7/0002* (2013.01); *G01B 11/24* (2013.01); *G06T 2207/30108* (2013.01)

(58) Field of Classification Search
CPC ......... G06T 2207/30108; G06T 7/0002; G06T 7/0004; G01N 21/952
See application file for complete search history.

(56) References Cited

U.S. PATENT DOCUMENTS

| | | | |
|---|---|---|---|
| 3,932,042 A | 1/1976 | Faani et al. | |
| 5,131,755 A | 7/1992 | Chadwick et al. | |
| 5,448,362 A | 9/1995 | Perchak | |
| 5,448,365 A * | 9/1995 | Grollimund | A24C 5/3412 250/239 |
| 5,712,701 A | 1/1998 | Clementi et al. | |
| 5,936,725 A * | 8/1999 | Pike | G01B 11/08 348/125 |
| 6,516,083 B1 * | 2/2003 | Bonechi | G01N 21/952 131/280 |
| 6,633,383 B1 | 10/2003 | Jackson et al. | |
| 2008/0013820 A1 * | 1/2008 | Vertoprakhov | G01N 21/8806 382/141 |

(Continued)

FOREIGN PATENT DOCUMENTS

| | | |
|---|---|---|
| JP | H0944624 A | 2/1996 |
| WO | 2013/080278 A1 | 6/2013 |

OTHER PUBLICATIONS

Thingiverse, "Filament Width Sensor with 3 LEDs, TSL1401CL, and Arduino Pro Micro," Published Mar. 3, 2015.

(Continued)

*Primary Examiner* — Maurice C Smith
(74) *Attorney, Agent, or Firm* — McGeary Cukor LLC; Jason Paul DeMont; Kenneth Ottesen

(57) ABSTRACT

A filament inspection system is disclosed that gathers empirical data on the physical and chemical properties of filament. The illustrative embodiments need only a single video camera and two mirrors to image all of the exterior surfaces of one or more filaments simultaneously. These images can be used to analyze the physical properties of the filament. Furthermore, the illustrative embodiments need only a simple electrical network to gather empirical data on the permittivity of each segment of filament, which gives insights into the chemical properties of the filament. For example, embodiments of the present invention are particularly well suited for inspecting fiber-reinforced thermoplastic filament, and variations in the number, dispersion, wetting, and length of the fibers are all observable in variations in permittivity.

18 Claims, 31 Drawing Sheets

(56) References Cited

U.S. PATENT DOCUMENTS

2017/0032516 A1* 2/2017 Luup .................... B07C 5/34

OTHER PUBLICATIONS

WO 2013/080278 A1, "Method of Inspecting Size of Filament Material and Inspection System for Same," Published, Jun. 6, 2013, K Nagato, English Translation by Google Patents.
JP H09442624A, "Filament Inspecting Device," Published Feb. 14, 1997, T. Ota, English Translation by Google Patents.

\* cited by examiner

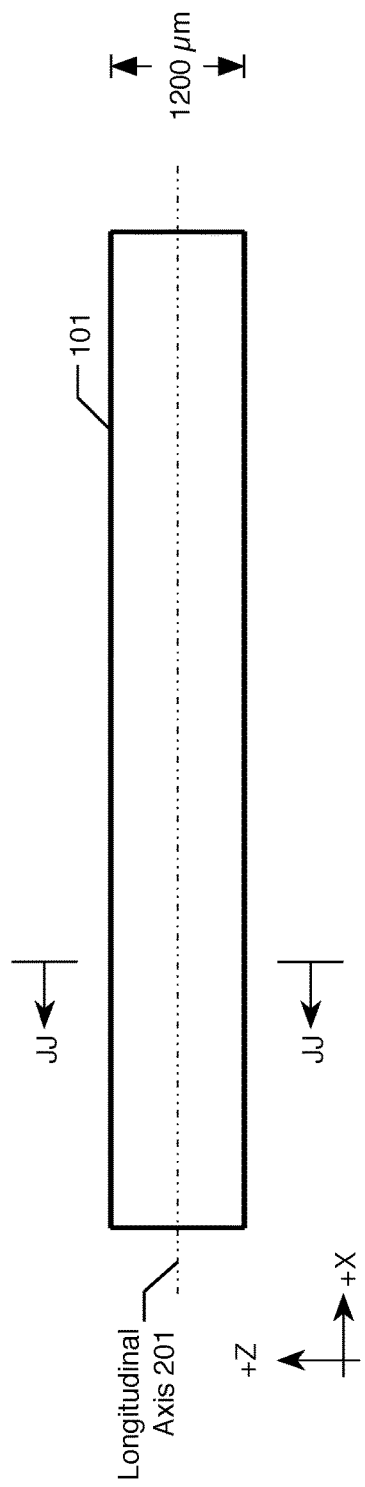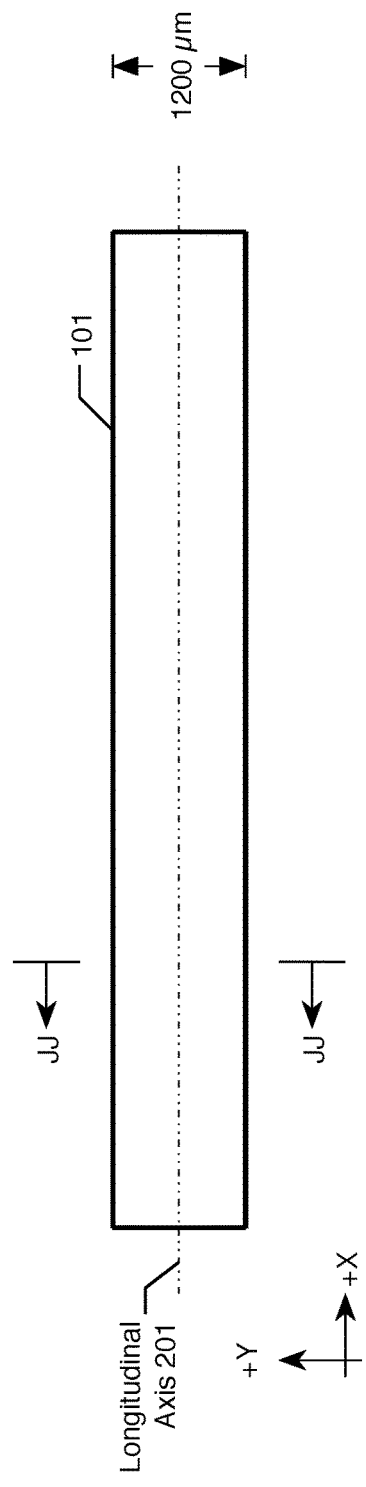

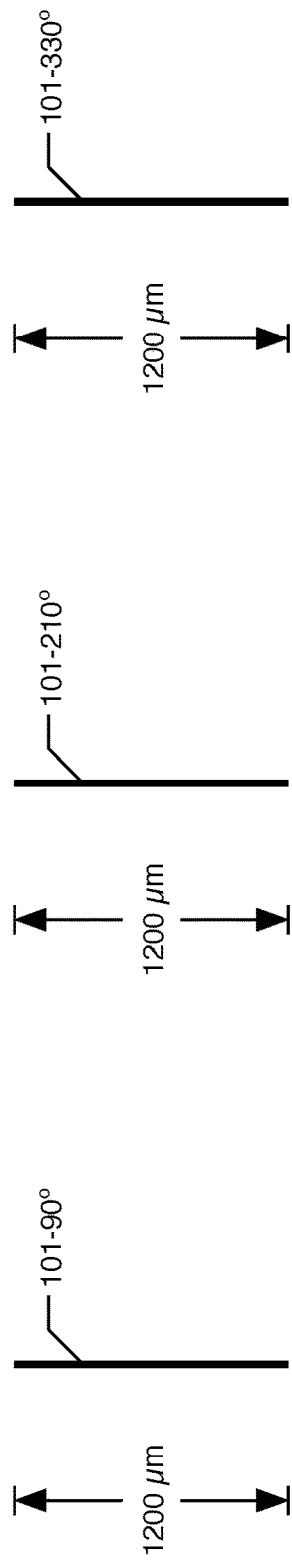

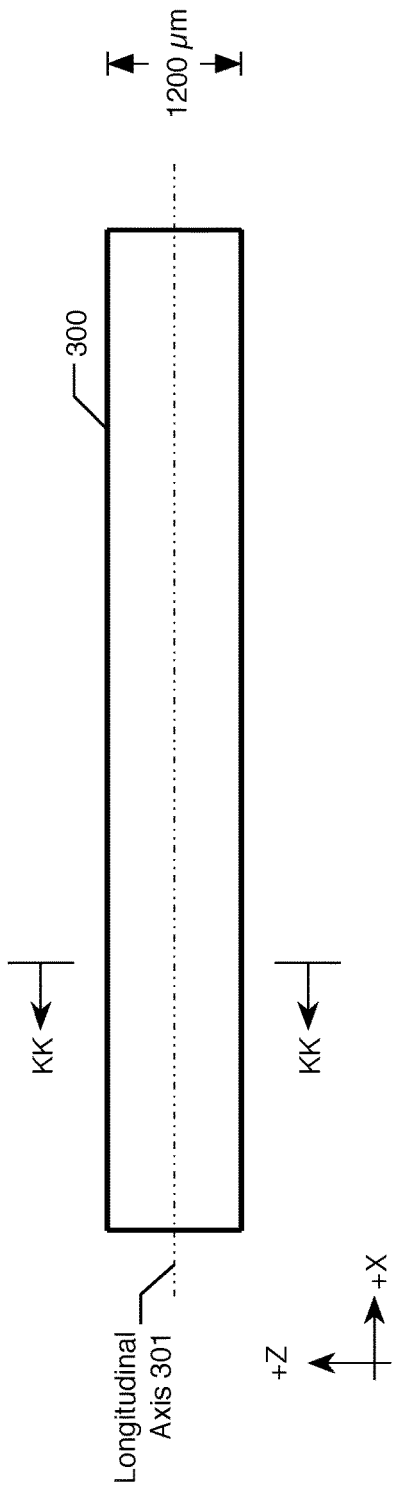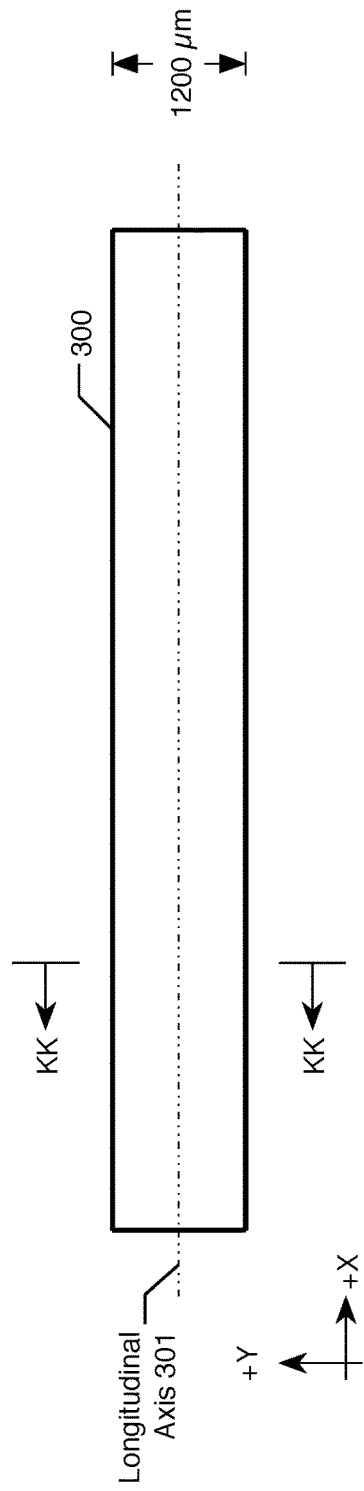

Radial Profile of Segment of Filament 101 from 330° Radial Perspective

Radial Profile of Segment of Filament 401 from 210° Radial Perspective

Radial Profile of Segment of Filament 401 from 90° Radial Perspective

Single-Filament Optical Sensor 121 w/o Filament 101
(Orthographic Side View)

Single-Filament Optical Sensor 121 w/o Filament 101
(Orthographic Side View Along Cross-Section YY-YY)

Single-Filament Optical Sensor 121 w/ Filament 101
(Orthographic Side View)

Single-Filament Optical Sensor 121 w/ Filament 101
(Orthographic Side View Along Cross-Section ZZ-ZZ)

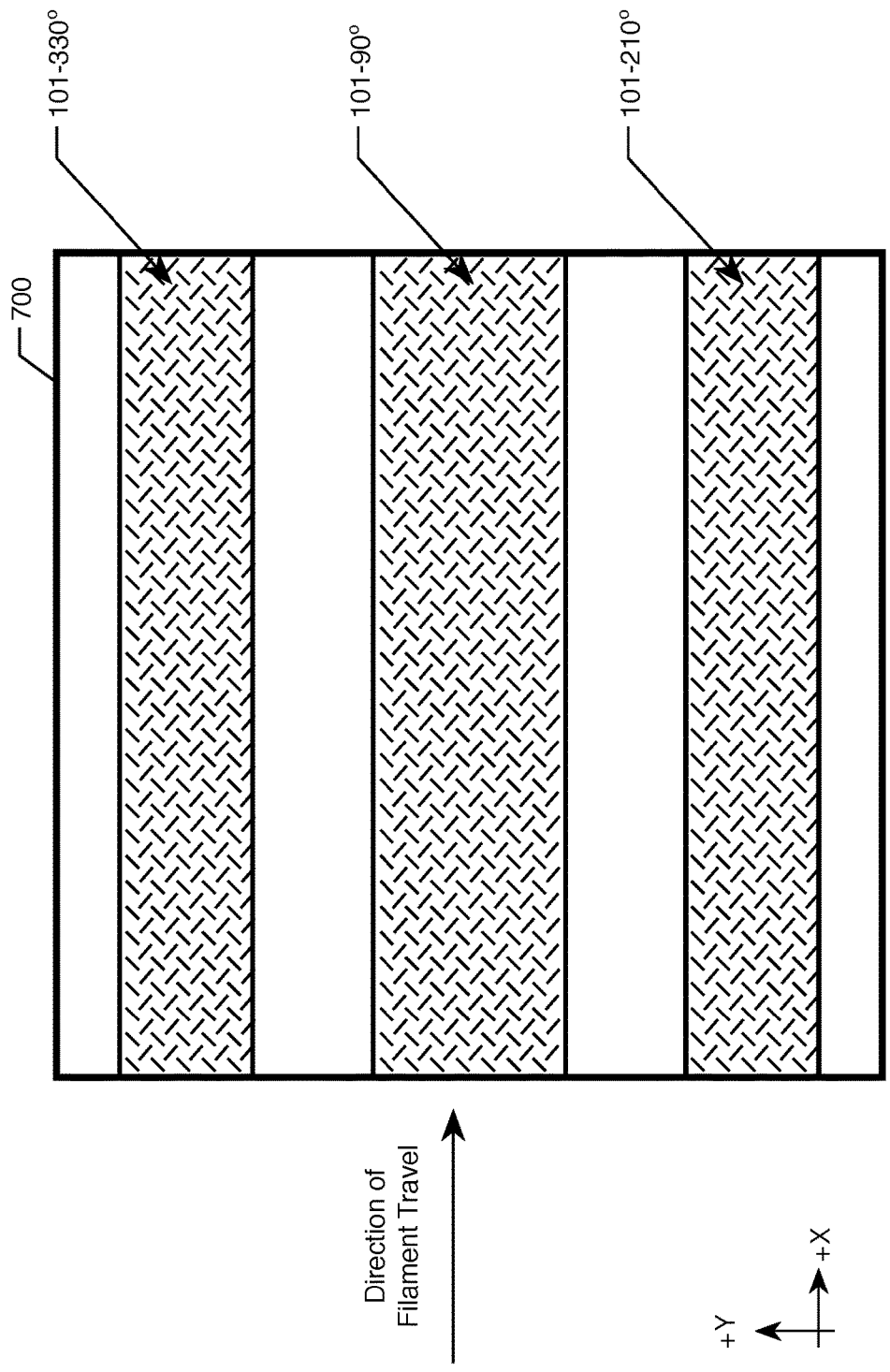

FILAMENT INSPECTION SYSTEM

FIELD OF THE INVENTION

The present invention relates to filament in general, and, more particularly, to a system for inspecting the physical and chemical properties of filament.

BACKGROUND OF THE INVENTION

The feedstock for many 3D printers is thermoplastic filament, and the physical and chemical characteristics of the filament limit the quality of an article that can be printed with it. Furthermore, the physical and chemical characteristics of the filament can vary along the length of the filament, and, therefore, it is advantageous to inspect each segment of the filament to ensure that it is within specification. When the filament contains too many segments that are out of specification, the entire filament is discarded, recycled, or used in making non-critical parts. In contrast, when only sporadic segments are out of specification, they can be cut out. In any case, the need exists for an inexpensive filament inspection system that can characterize the physical and chemical properties of each segment of a filament.

BRIEF SUMMARY OF THE INVENTION

The present invention enables the making and using of filament inspection systems that avoid some of the costs and disadvantages of filament inspection systems in the prior art. In particular, embodiments of the present invention can be less expensive than filament inspection systems in the prior art.

The illustrative embodiments need only a single video camera and two mirrors to image all of the exterior surfaces of one or more filaments simultaneously. These images can be used to analyze the physical properties of the filament. Furthermore, the illustrative embodiments need only a simple electrical network to gather empirical data on the permittivity of each segment of filament, which gives insights into the chemical properties of the filament. For example, embodiments of the present invention are particularly well suited for inspecting fiber-reinforced thermoplastic filament, and variations in the number, dispersion, wetting, and length of the fibers are all observable in variations in permittivity.

One of the illustrative embodiments comprises:

a first mirror;

a second mirror;

a first filament guide and a second filament guide capable of positioning a filament in a path, wherein the path comprises a longitudinal axis at a point;

a camera capable of generating a video frame that comprises:

(1) a first image of a first radial profile of a segment of the filament in the path from a first radial perspective, and (2) a second image of a second radial profile of the segment of the filament in the path from a second radial perspective, wherein the second image is received by the camera via reflection in the first mirror, and (3) a third image of a third radial profile of the segment of the filament in the path from a third radial perspective, wherein the third image is reflected into the camera by the second mirror; and a support structure for establishing and maintaining the relative spatial relationship of the first mirror, the second mirror, the first filament guide, the second filament guide, and the camera.

BRIEF DESCRIPTION OF THE DRAWINGS

FIG. 2a depicts an orthographic front view of a segment of filament 101.

FIG. 2b depicts an orthographic top view of a segment of filament 101.

FIG. 2d depicts an orthographic radial profile of filament 101 at cross-section JJ-JJ from the 90° radial perspective.

FIG. 2e depicts an orthographic radial profile of filament 101 at cross-section JJ-JJ from the 210° radial perspective.

FIG. 2f depicts an orthographic radial profile of filament 101 at cross-section JJ-JJ from the 330° radial perspective.

FIG. 3a depicts an orthographic front view of a segment of filament 300, which has a square cross-section.

FIG. 3b depicts an orthographic top view of a segment of filament 300, which has a square cross-section.

FIG. 8 depicts one frame of the video feed from single-filament optical sensor 121, which frame comprises filament image 101—90°, filament image 101—210°, and filament image 101—330°.

DETAILED DESCRIPTION

Figure 1:
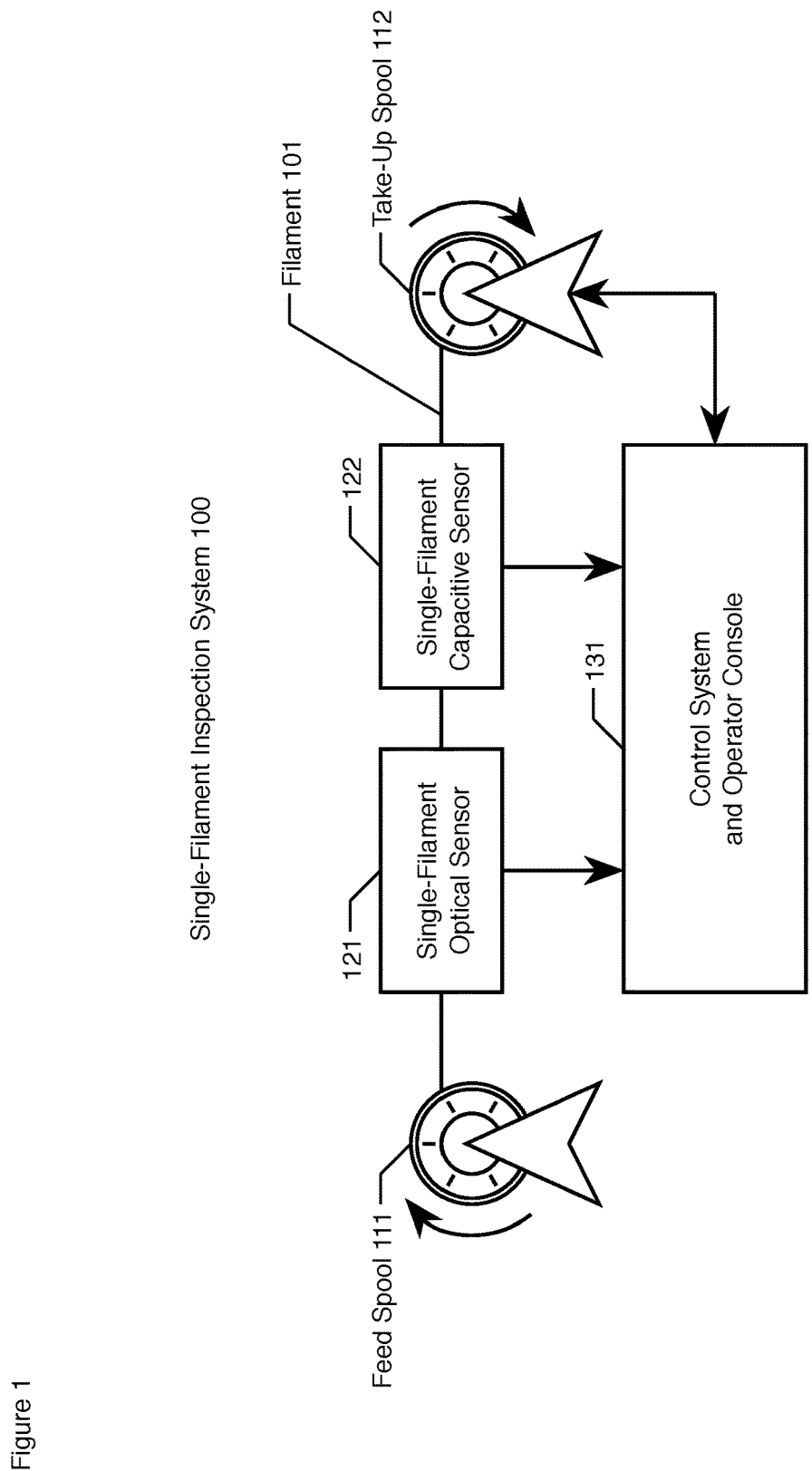
FIG. 1 depicts a schematic diagram of the salient components of Single-Filament Inspection System 100, in accordance with the first illustrative embodiment of the present invention.

FIG. 1 depicts a schematic diagram of the salient components of single-filament inspection system 100. System 100 comprises: filament 101, feed spool 111, take-up spool 112, single-filament optical sensor 121, single-filament capacitive sensor 122, and control system and operator console 131. In accordance with the illustrative embodiment, filament 101 is unspooled from feed spool 111, fed through single-filament optical sensor 121 and single-filament capacitive sensor 122, and re-spooled onto take-up spool 112, all under the direction and supervision of control system and operator console 131.

Filament 101 is a single thin length of material that is 3000 meters long. The goal in manufacturing filament 101 is to make its physical properties (e.g., cross-section, chemical composition, void content, fiber content, fiber distribution, etc.) uniform along its length. In practice, however, its physical properties can and do vary along its length and the purpose of filament inspection system 100 is to measure its physical properties at each location along its length. Filament 101 is described in detail below and in the accompanying figures.

Take-up spool 112 is a metal reel that holds 3000 meters of filament 101 and that comprises a motor (not shown in FIG. 1) that winds filament 101 at 7 mm per second. In accordance with the first illustrative embodiment, take-up spool 112 holds 3000 meters of filament 101, but it will be clear to those skilled in the art, after reading this disclosure, how to make and use alternative embodiments of the present invention in which the spool has a different capacity. In accordance with the first illustrative embodiment, filament 101 is drawn through single-filament optical sensor 121 and single-element capacitive sensor 122 and wound onto take-up spool 112 at the rate of 7 mm per second, but it will be clear to those skilled in the art how to make and use alternative embodiments of the present invention in which the filament is wound and inspected at a different rate. In any case, it will be clear to those skilled in the art how to make and use take-up spool 112.

Feed spool 111 is a metal reel that holds 3000 meters of filament 101. Filament 101 is pulled off of feed spool 111 (by take-up spool 112) and feed spool 111 comprises a tensioning device (not shown in FIG. 1) that maintains the tension on filament 101 through single-filament optical sensor 121 and single-filament capacitive sensor 122 at approximately 50 Newtons. In accordance with the first illustrative embodiment, feed spool 111 holds 3000 meters of filament 101, but it will be clear to those skilled in the art, after reading this disclosure, how to make and use alternative embodiments of the present invention in which the spool has a different capacity. In accordance with the first illustrative embodiment, feed spool 111 maintains filament 101 at approximately 50 Newtons of tension, but it will be clear to those skilled in the art, after reading this disclosure, how to make and use alternative embodiments of the present invention in which the filament is kept at a different tension. In any case, it will be clear to those skilled in the art how to make and use take-up spool 112.

Figure 2C:
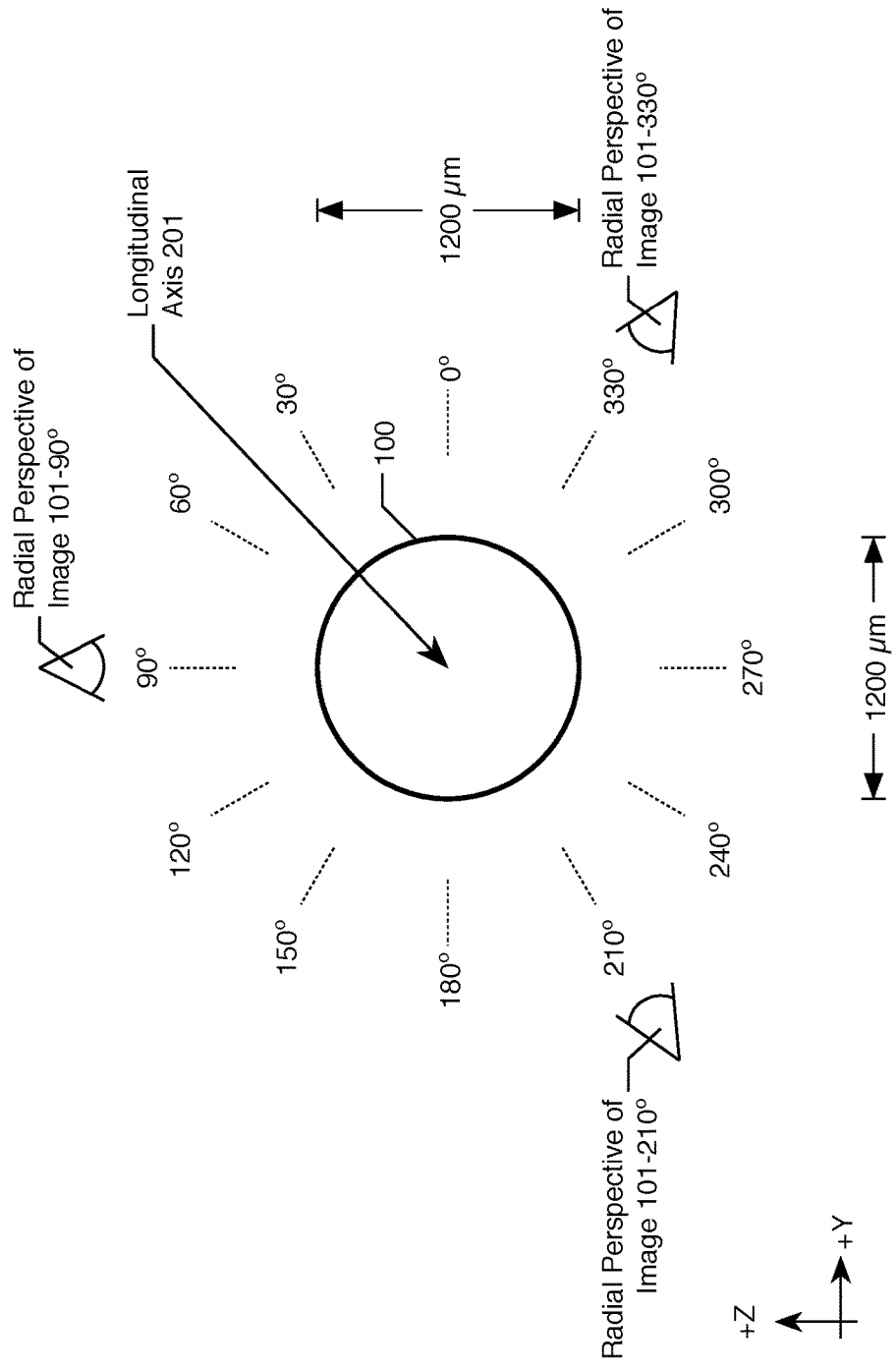
FIG. 2c depicts an orthographic side view of a segment of filament 101.
Figure 7A:
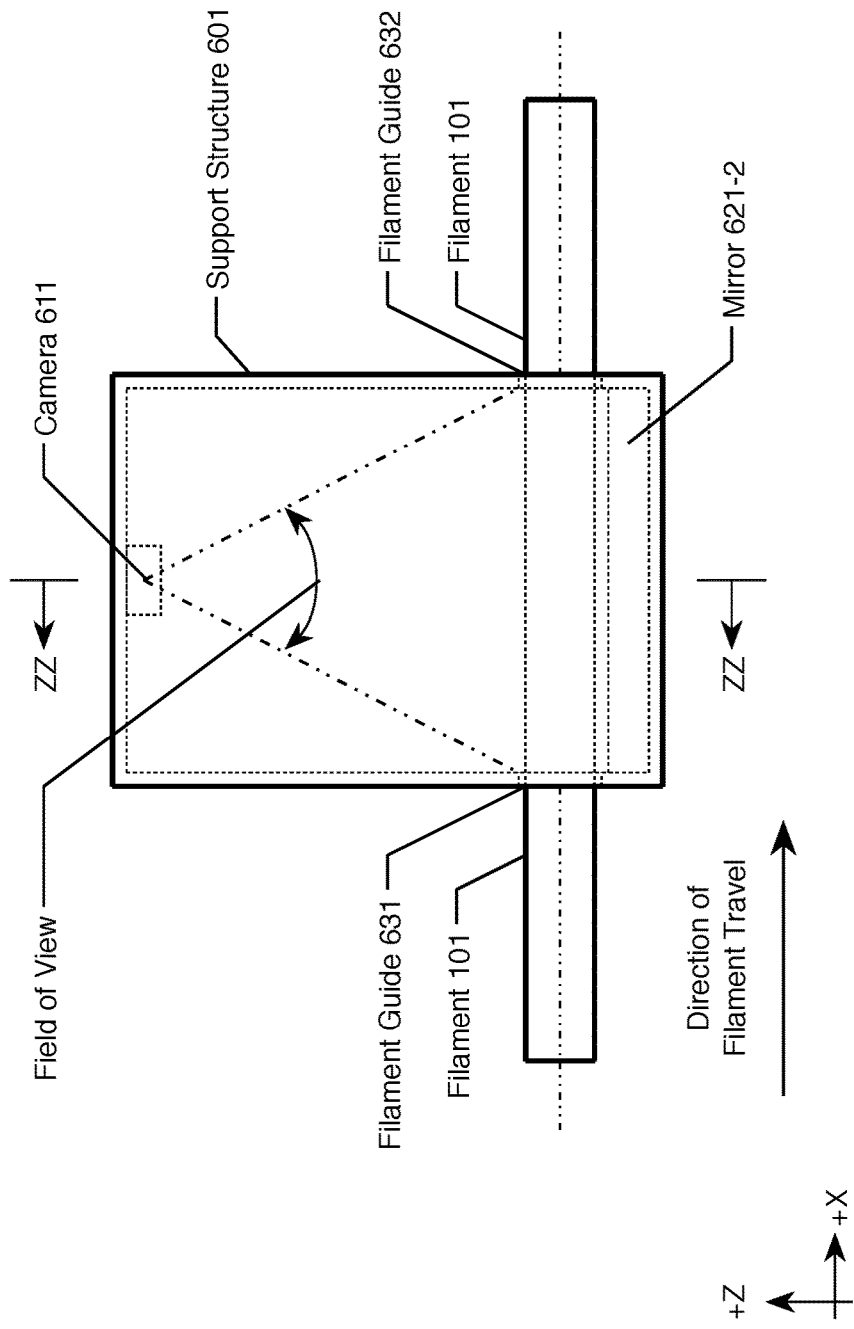
FIG. 7a depicts the front orthographic view of the salient components of single-filament optical sensor 121 in accordance with the illustrative embodiments of the present invention with filament 101.
Figure 7B:
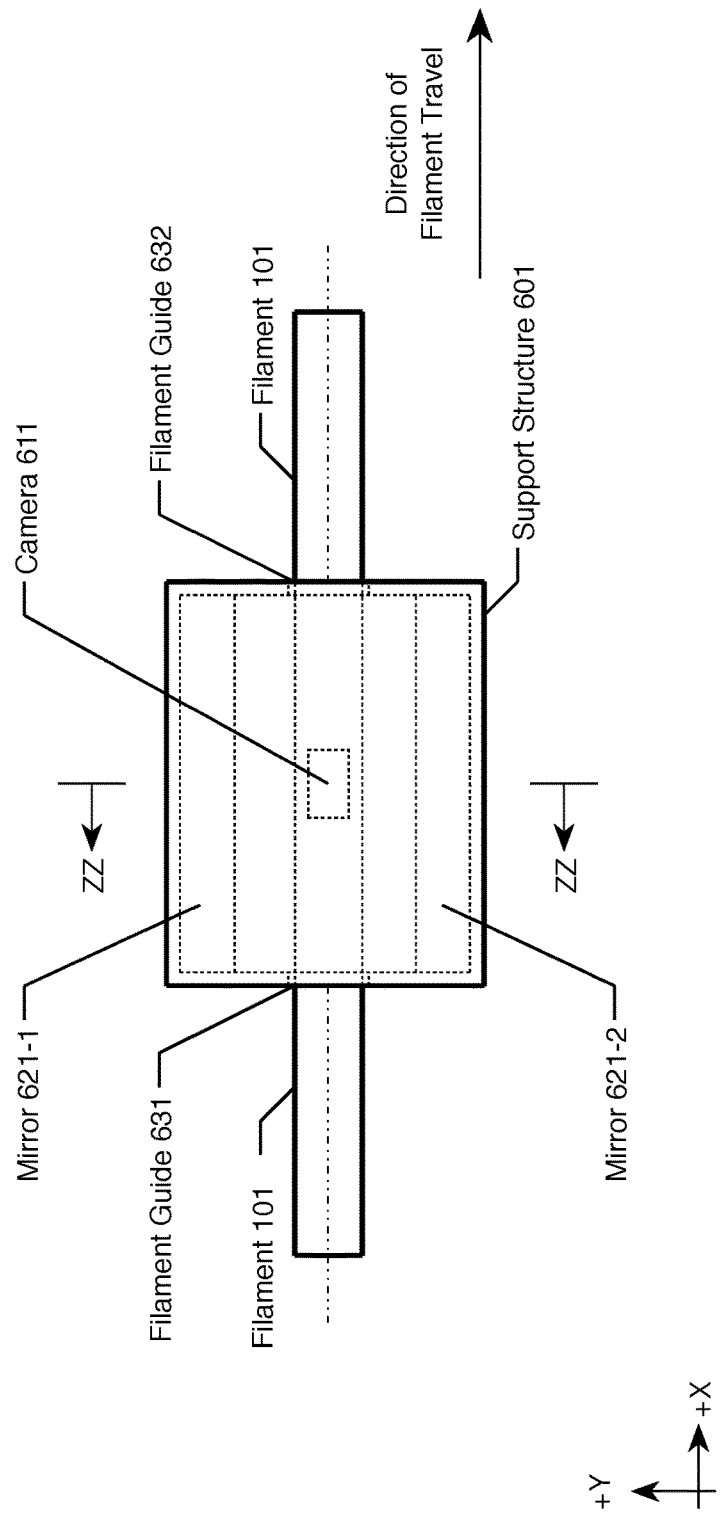
FIG. 7b depicts the top orthographic view of the salient components of single-filament optical sensor 121 in accordance with the illustrative embodiments of the present invention with filament 101.
Figure 7C:
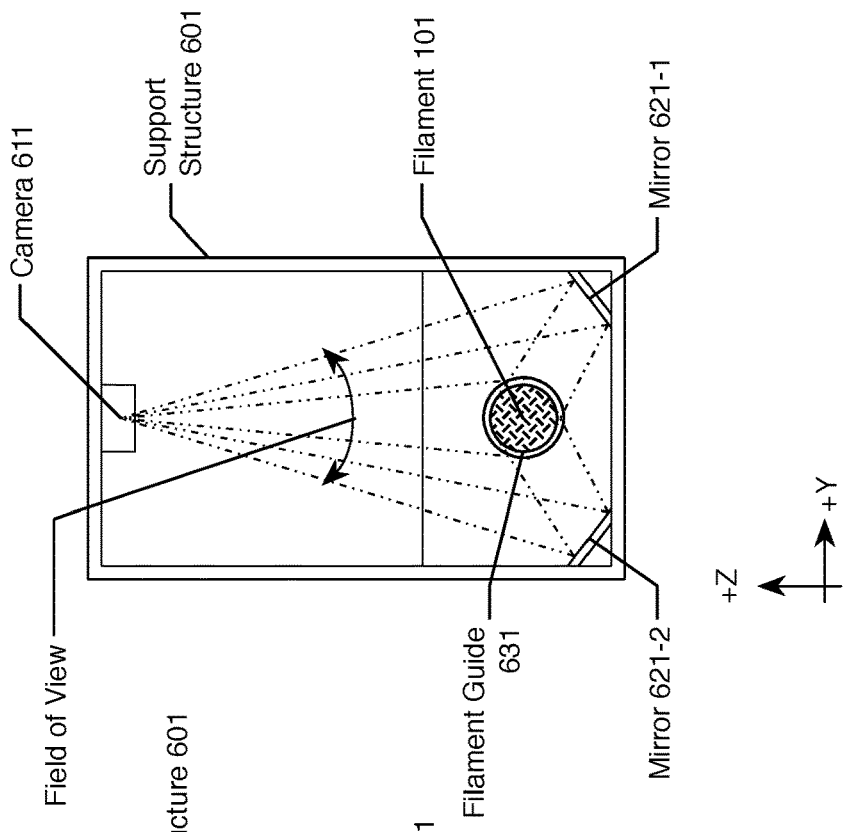
FIG. 7c depicts the side orthographic view of the salient components of single-filament optical sensor 121 in accordance with the illustrative embodiments of the present invention with filament 101.
Figure 7D:
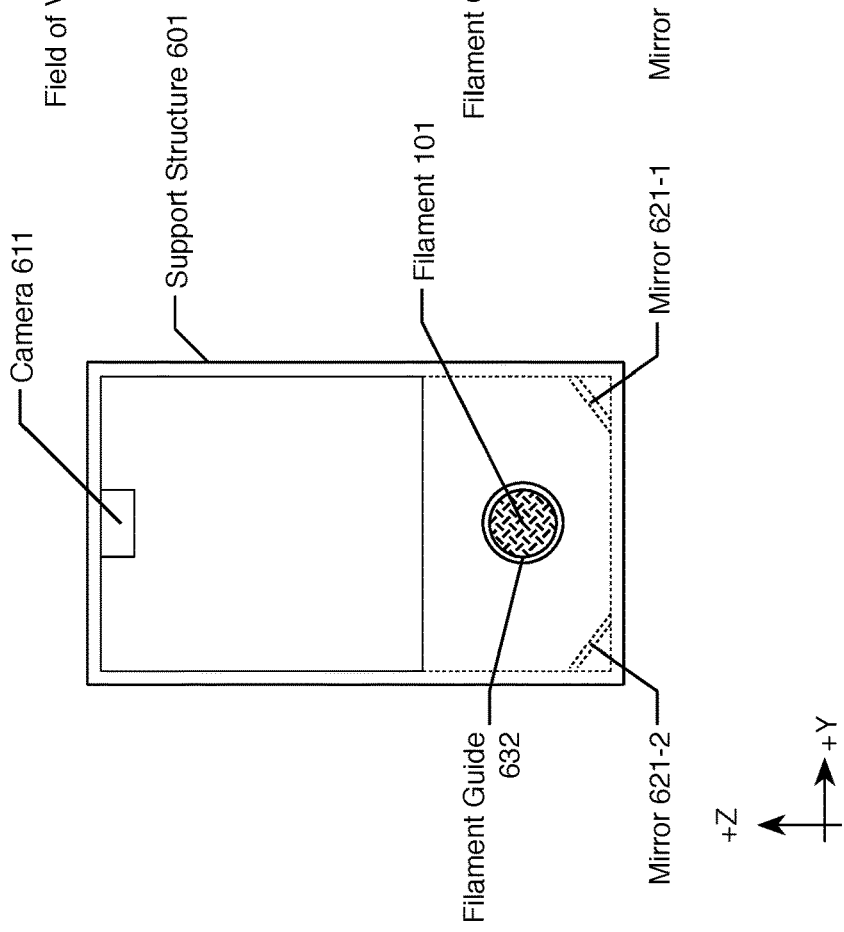
FIG. 7d depict an orthographic side view—along cross-section ZZ-ZZ—of single-filament optical sensor 121 without filament 101.

Single-filament optical sensor 121 comprises a digital video camera that generates a high-resolution video signal in which each video frame (as shown in FIG. 8) embodies three different images of filament 101. In particular, each of the three images is an image of a different radial profile of filament 101 taken from a different radial perspective around the longitudinal axis of filament 101. For example (as shown in FIGS. 2c and 7d), one image—image 101—90° (shown in FIG. 2d)—is taken from the 90° radial perspective (as shown in FIG. 2c); one image—image 101—210° (shown in FIG. 2e)—is taken from the 210° radial perspective (as shown in FIG. 2c), and one image—image 101—330°—is taken from the 330° radial perspective (as shown in FIG. 2f). Among other things, each of the three images depicts the width of filament 101 from three different perspectives. The video signal from single-filament optical sensor 121 is provided, in well-known fashion, to control system and operator console 131 for analysis and processing. Single-filament optical sensor 121 is described in detail below and in the accompanying figures.

Single-filament capacitive sensor 122 comprises hardware and software that gathers empirical data on the physical properties of filament 101 at every position along its length. In particular, single-filament capacitive sensor 122 comprises an electrical circuit that measures the permittivity of filament 101 at each location along its length.

Figure 13:
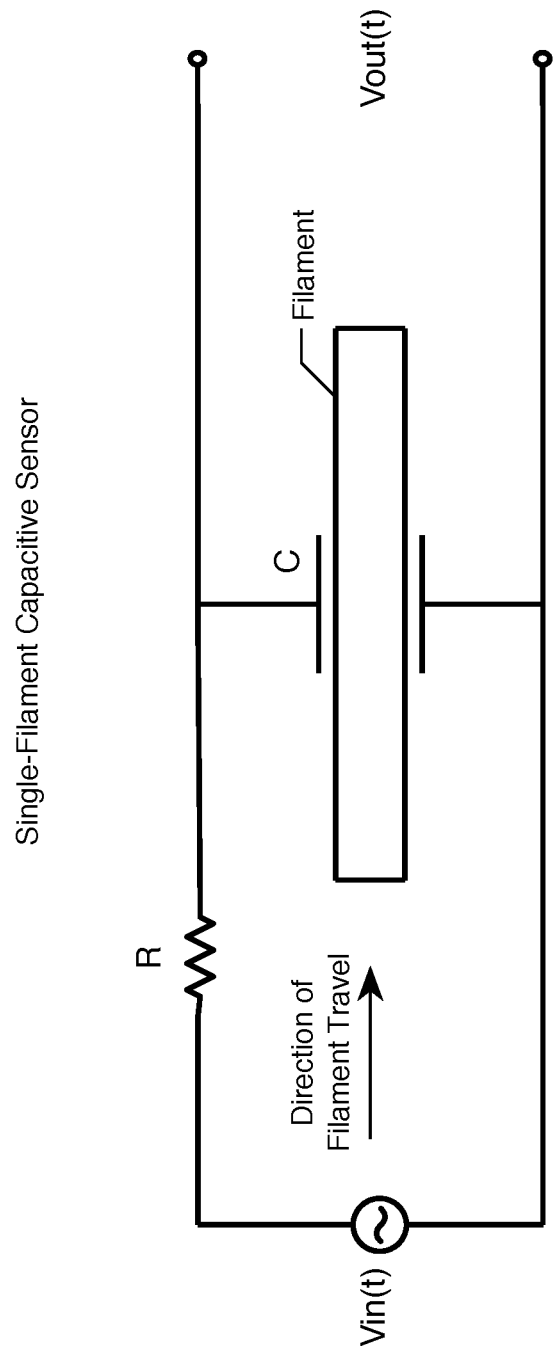
FIG. 13 depicts a schematic diagram of an electrical resistor-capacitor (hereinafter "RC") circuit that is capable of measuring the permittivity e of a segment of filament 101.

For example, FIG. 13 depicts a schematic diagram of an electrical resistor-capacitor (hereinafter "RC") circuit that is capable of measuring the permittivity E of a segment of filament 101. In accordance with the RC circuit in FIG. 13, successive segments of filament 101 pass between two flat square parallel metal plates. Each metal plate has a surface area A and the plates are a distance d apart. The capacitance C of the metal plates and the segment of filament 101 currently between the plates is a function of the permittivity E of the segment:

$$C = \frac{\epsilon A}{d} \quad \text{(Eq. 1)}$$

As is well known to those skilled in the art, the capacitance C can be determined by applying a time-varying voltage Vin(t) to the circuit and measuring the resulting voltage across the capacitor. As is well known to those skilled in the art, the capacitance C can be determined from the function:

$$Vout(t) = \frac{1}{1 + RC} Vin(t) \quad \text{(Eq. 2)}$$

It will be clear to those skilled in the art, after reading this disclosure, how to use other RC circuits to measure the permittivity of filament 101. Variations in the permittivity of filament 101 along its length are indicative of variations in the physical properties of filament 101 along its length. The measure of the permittivity of each segment of filament 101 is continuously provided, in well-known fashion, to control system and operator console 131 for analysis and processing. It will be clear to those skilled in the art how to make and use single-filament capacitive sensor 122.

Control system and operator console 131 comprises hardware and software to:
 (i) control the unspooling and spooling of filament 101, and
 (ii) receive, process, and interpret the images of the various radial profiles in the stream of video frames from single-filament optical sensor 121, and
 (iii) receive, process, and interpret the permittivity measurements from single-filament capacitive sensor 122, and
 (iv) interact with a human operator (who is not shown in FIG. 1), and
 (v) determine the physical properties of each segment of filament 101, and
 (vi) determine whether the physical and chemical properties of each segment of filament 101 are within specification tolerance, and
 (vii) to associate each position along the 3000 meters of filament 101 with those physical properties.

It will be clear to those skilled in the art, after reading this disclosure, how to make and use control system and operator console 131.

FIGS. 2a, 2b, and 2c depict orthographic front, top, and side views, respectively, of a segment of filament 101. FIGS. 2d, 2e, and 2f depict orthographic radial profiles of filament 101 at cross-section JJ-JJ from 90° radial perspective, 210° radial perspective, and 330° radial perspective, respectively.

In accordance with the illustrative embodiments, filament 101 comprises a single thin length of material with a (generally) circular cross-section that is approximately 1200 μm in diameter. Filament 101 comprises a longitudinal axis—longitudinal axis 201—along its entire length.

In accordance with the illustrative embodiments, filament 101 comprises a tow of reinforcing fibers, which fibers are substantially parallel to longitudinal axis 201. In particular, filament 101 comprises a cylindrical towpreg of continuous 12K carbon fiber that is impregnated with thermoplastic resin.

In accordance with the illustrative embodiments, filament 101 comprises a tow of 12K fibers, but it will be clear to those skilled in the art, after reading this disclosure, how to make and use alternative embodiments of the present invention in which the tow comprises a different number of fibers (e.g., 1K, 3K, 6K, 24K, etc.).

In accordance with the illustrative embodiments, filament 101 comprises carbon fibers, but it will be clear to those skilled in the art, after reading this disclosure, how to make and use alternative embodiments of the present invention in which the fibers are made of a different material. For example:
 (i) fiberglass, or
 (ii) aramid, or
 (iii) metal, or
 (iv) carbon, or
 (v) any combination of i, ii, iii, and iv.

In accordance with the illustrative embodiments, filament 101 comprises continuous carbon fibers, but it will be clear to those skilled in the art, after reading this disclosure, how to make and use alternative embodiments of the present invention in which the filament comprises:
 (i) chopped fibers 1 mm), or
 (ii) short fibers (1 mm to 10 mm), or
 (iii) long fibers (10 mm to 100 mm), or
 (iv) "continuous" fibers (>100 mm), or
 (v) any combination of i, ii, iii, and iv.

Figure 3C:
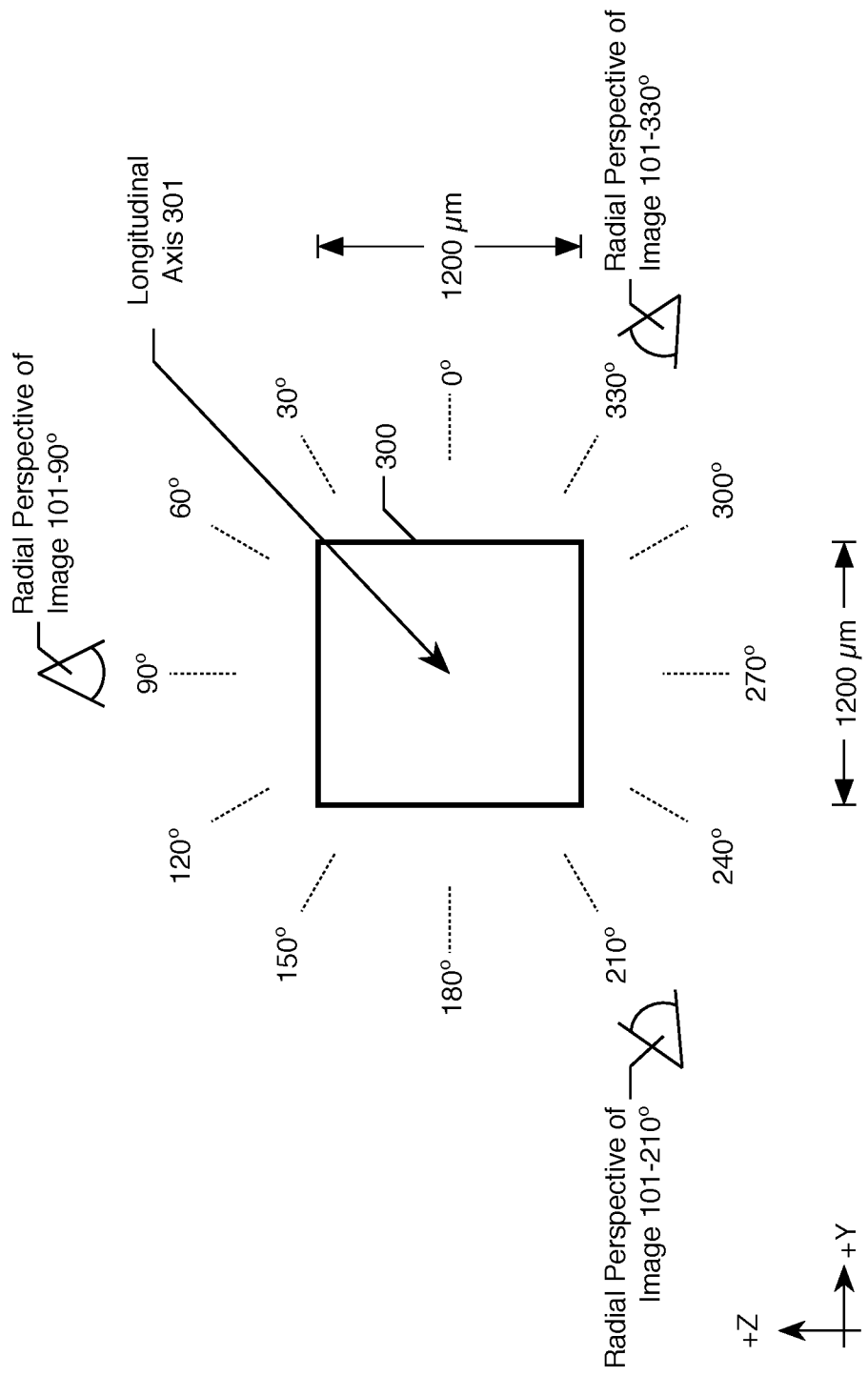
FIG. 3c depicts an orthographic side view of a segment of filament 300, which has a square cross-section.

In accordance with the illustrative embodiments, filament 101 has a circular cross-section, but it will be clear to those skilled in the art, after reading this disclosure, how to make and use alternative embodiments of the present invention in which the filament has a different cross-section (e.g., an equilateral triangle, an isosceles triangle, a scalene triangle, a square, a rhombus, a rectangle, a parallelogram, an isosceles trapezoid, an irregular trapezoid, a kite, an irregular quadrilateral, a regular pentagon, an irregular pentagon, a concave pentagon, a convex pentagon, a regular hexagon, an irregular hexagon, a concave hexagon, a convex hexagon, etc.) For example, FIGS. 3a, 3b, and 3c depict orthographic front, top, and side views, respectively, of a segment of filament 300, which has a square cross-section with a side of 1200 μm and a longitudinal axis 301.

Figure 4A:
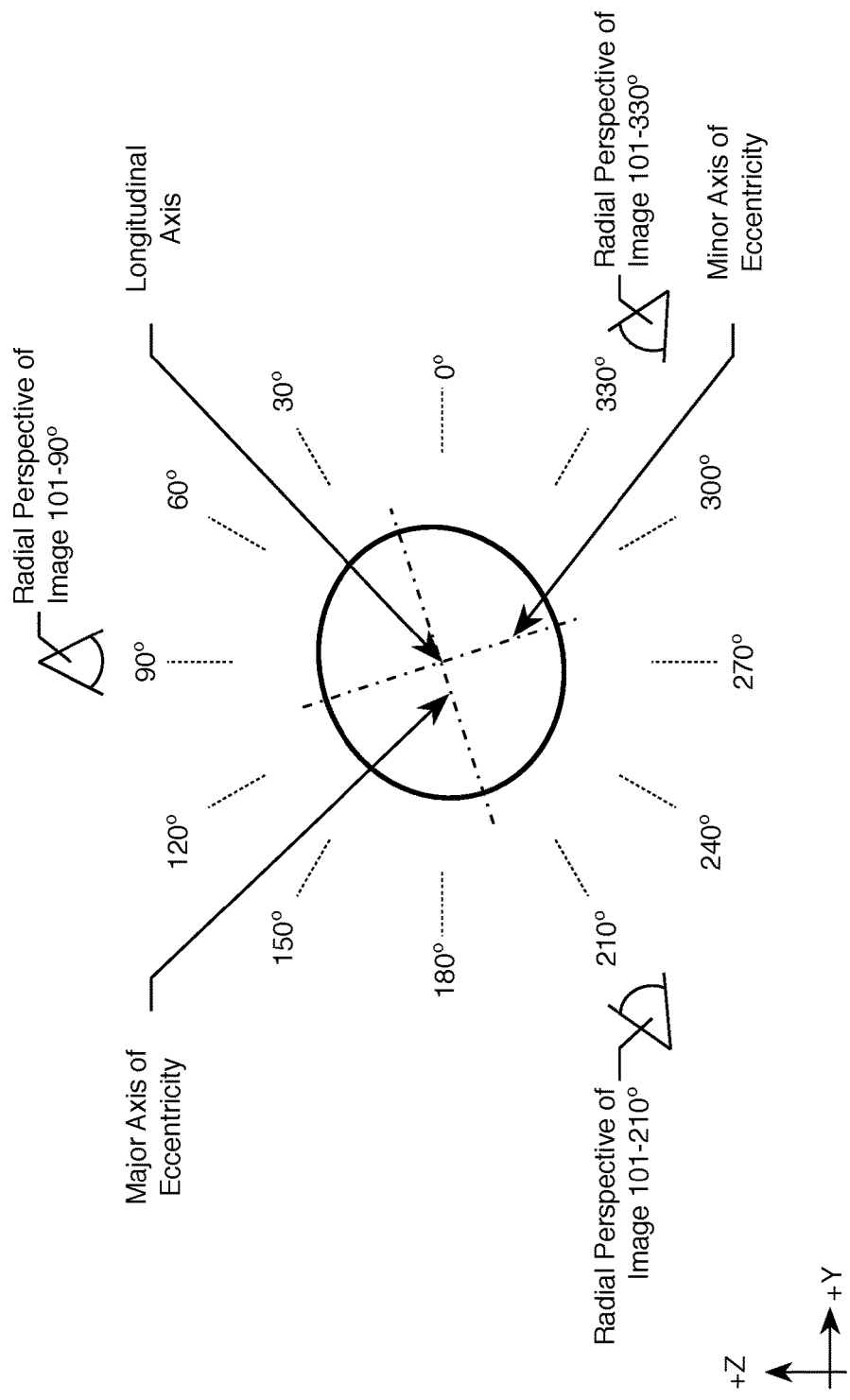
FIG. 4a depicts an orthographic side view of a cross-section of a deformed circular filament.
Figure 4D:
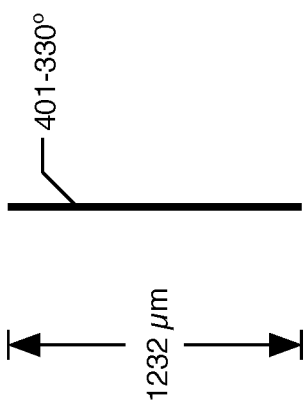
FIG. 4d depicts an orthographic radial profile of filament 401 from the 330° radial perspective.
Figure 4C:
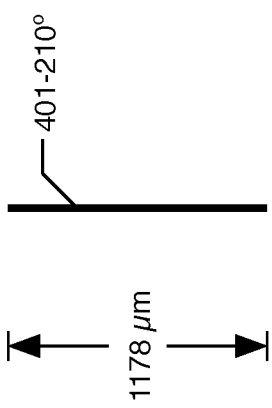
FIG. 4c depicts an orthographic radial profile of filament 401 from the 210° radial perspective.
Figure 4B:
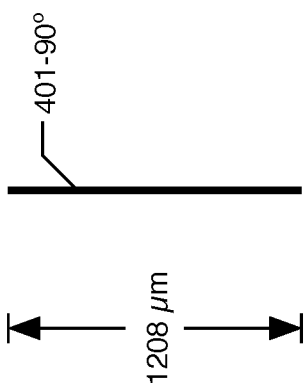
FIG. 4b depicts an orthographic radial profile of filament 401 from the 90° radial perspective.

In accordance with the illustrative embodiments, various positions along the length of filament 101 comprise cross-section deformations (i.e., positions where the cross-section is not perfectly circular) and other structural defects (e.g., large voids, fiber leakage (i.e., "fuzz" emanating from the surface of filament 101), insufficient wetting of fibers, insufficient number of fibers, unacceptable number of broken fibers, insufficient fiber dispersal, etc.). The deformations and other structural defects are due to imperfections in the manufacturing of filament 101. For example, FIG. 4a depicts an orthographic side view of a cross-section of deformed circular filament in which the actual cross-section is elliptical with a major axis at 18° and a length of 1260 µm and a minor axis at 180° and a length of 1140 µm. FIGS. 4*b*, 4*c*, and 4*d* depict orthographic radial profiles of filament 401 from the 90° radial perspective, the 210° radial perspective, and the 330° radial perspective, respectively. By measuring the three radial profiles of filament 401, it will be clear to those skilled in the art how to enable control system and operator control 131 to estimate whether or not the cross-section of filament 401 is deformed (e.g., to estimate the eccentricity of the cross-section based on the three radial measurements, etc.).

Figure 5:
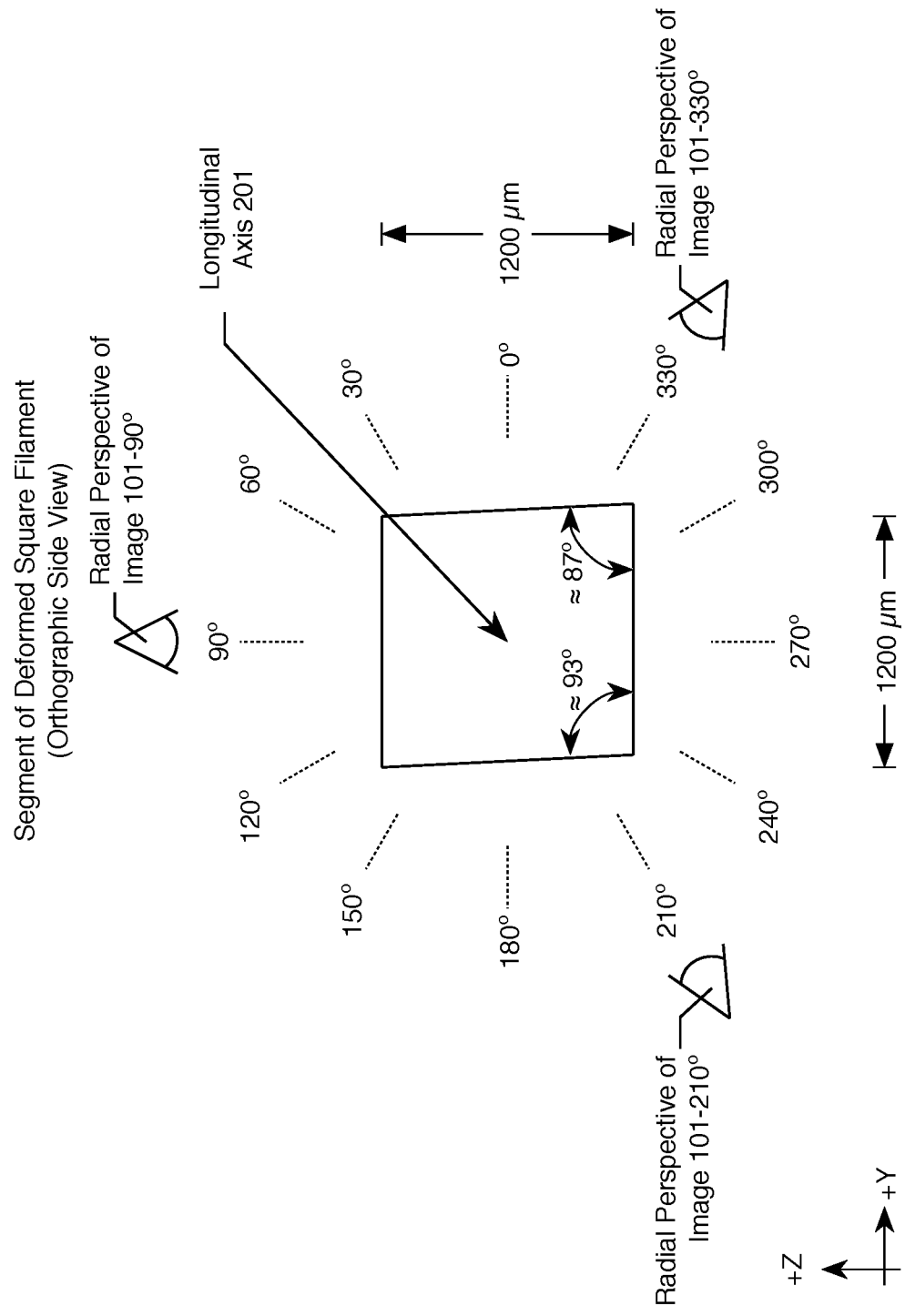
FIG. 5 depicts an orthographic side view of a cross-section of a deformed square filament in which the cross-section has deformed into a rhombus.

As another example, FIG. 5 depicts an orthographic side view of a cross-section of a deformed square filament in which the cross-section has deformed into a rhombus. It will be clear to those skilled in the art that there are an infinite number of different cross-section deformations. It will be clear to those skilled in the art, after reading this disclosure, how to make and use embodiments of the present invention that capture multiple radial profiles of a square filament, and, by measuring those profiles determines whether or not a cross-section of the square filament is deformed.

In accordance with the illustrative embodiments, the thermoplastic in filament 101 is, in general, a semi-crystalline polymer and, in particular, the polyaryletherketone (PAEK) known as polyetherketone (PEK). It will be clear to those skilled in the art, however, after reading this disclosure, how to make and use alternative embodiments of the present invention in which the semi-crystalline material is the polyaryletherketone (PAEK), polyetheretherketone (PEEK), polyetherketoneketone (PEKK), polyetheretherketoneketone (PEEKK), or polyetherketoneetherketoneketone (PEKEKK).

It will be clear to those skilled in the art, however, after reading this disclosure, how to make and use alternative embodiments of the present invention in which the semi-crystalline polymer is not a polyaryletherketone (PAEK) but another semi-crystalline thermoplastic (e.g., polyamide (PA), polybutylene terephthalate (PBT), poly(p-phenylene sulfide) (PPS), etc.) or a mixture of a semi-crystalline polymer and an amorphous polymer.

When the filament comprises a blend of an amorphous polymer with a semi-crystalline polymer, the semi-crystalline polymer can one of the aforementioned materials and the amorphous polymer can be a polyarylsulfone, such as polysulfone (PSU), polyethersulfone (PESU), polyphenylsulfone (PPSU), polyethersulfone (PES), or polyetherimide (PEI). In some additional embodiments, the amorphous polymer can be, for example and without limitation, polyphenylene oxides (PPOs), acrylonitrile butadiene styrene (ABS), methyl methacrylate acrylonitrile butadiene styrene copolymer (ABSi), polystyrene (PS), or polycarbonate (PC).

When the filament comprises a blend of an amorphous polymer with a semi-crystalline polymer, the weight ratio of semi-crystalline material to amorphous material can be in the range of about 50:50 to about 95:05, inclusive, or about 50:50 to about 90:10, inclusive. Preferably, the weight ratio of semi-crystalline material to amorphous material in the blend is between 60:40 and 80:20, inclusive. The ratio selected for any particular application may vary primarily as a function of the materials used and the properties desired for the printed article.

It will be clear to those skilled in the art, after reading this disclosure, how to make and use alternative embodiments of the present invention in which the filament comprises a metal. For example, and without limitation, the filament can comprise stainless steel, Inconel® (nickel/chrome), titanium, aluminum, cobalt chrome, copper, bronze, iron, precious metals (e.g., platinum, gold, silver, etc.).

Figure 6A:
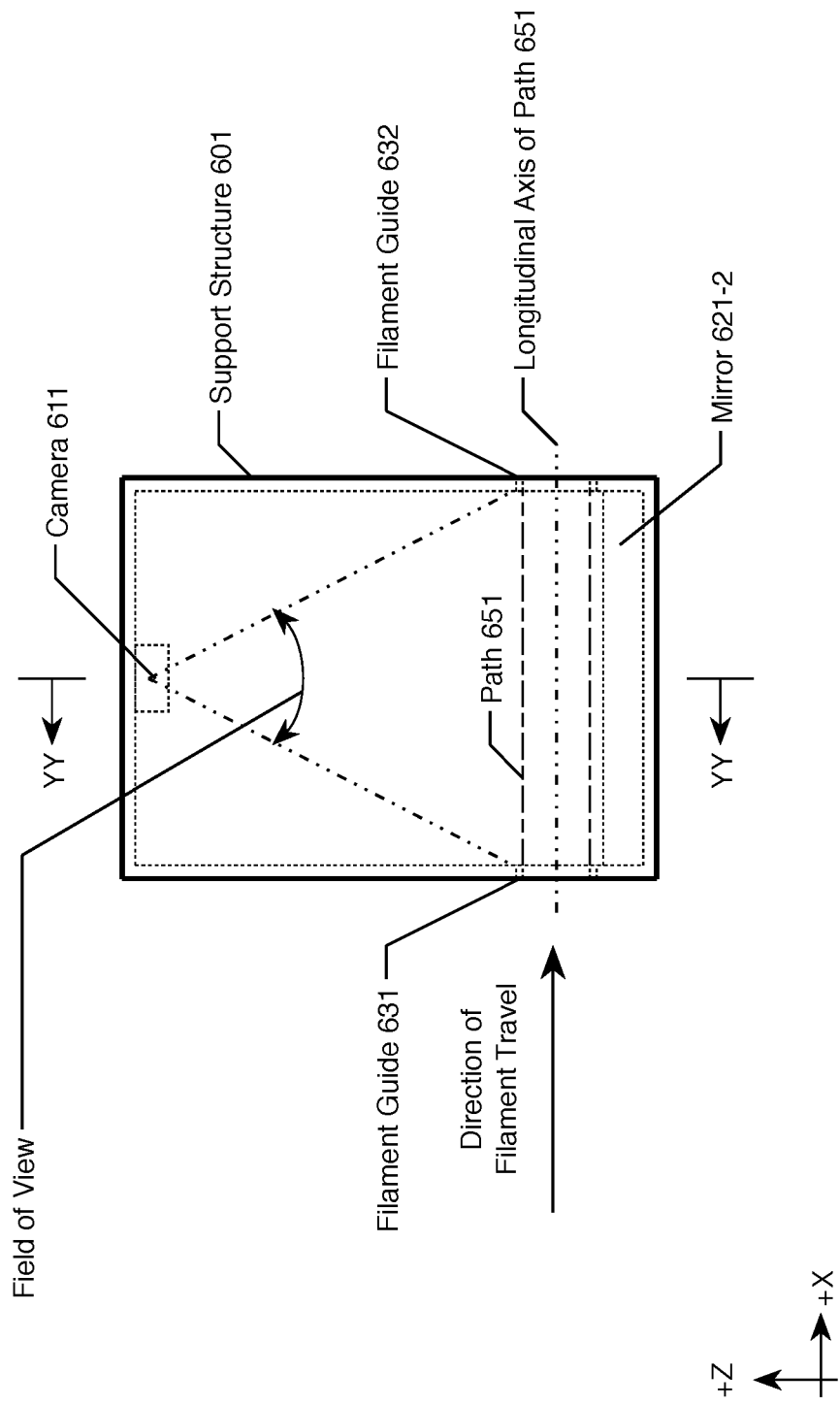
FIG. 6a depicts the front orthographic view of the salient components of single-filament optical sensor 121 in accordance with the illustrative embodiments of the present invention without filament 101.
Figure 6B:
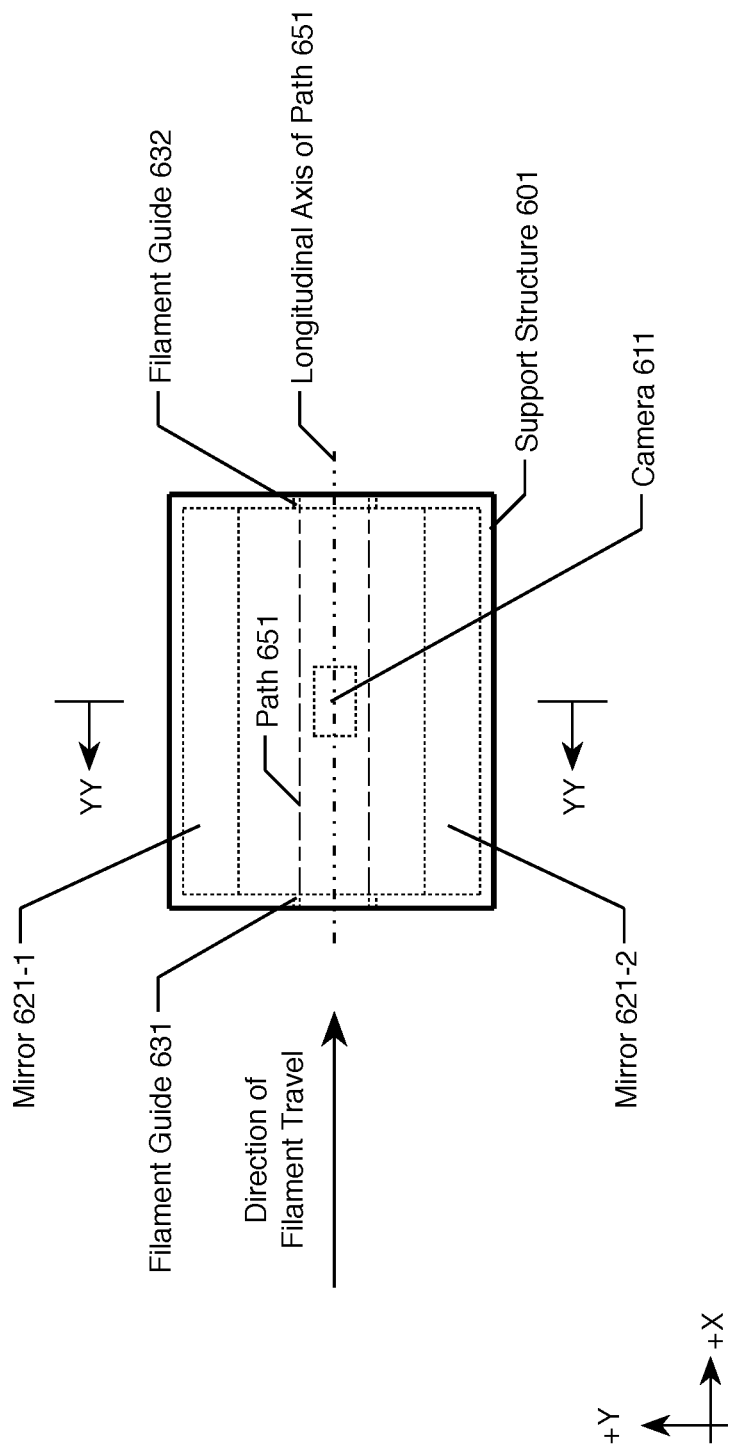
FIG. 6b depicts the top orthographic view of the salient components of single-filament optical sensor 121 in accordance with the illustrative embodiments of the present invention without filament 101.
Figure 6C:
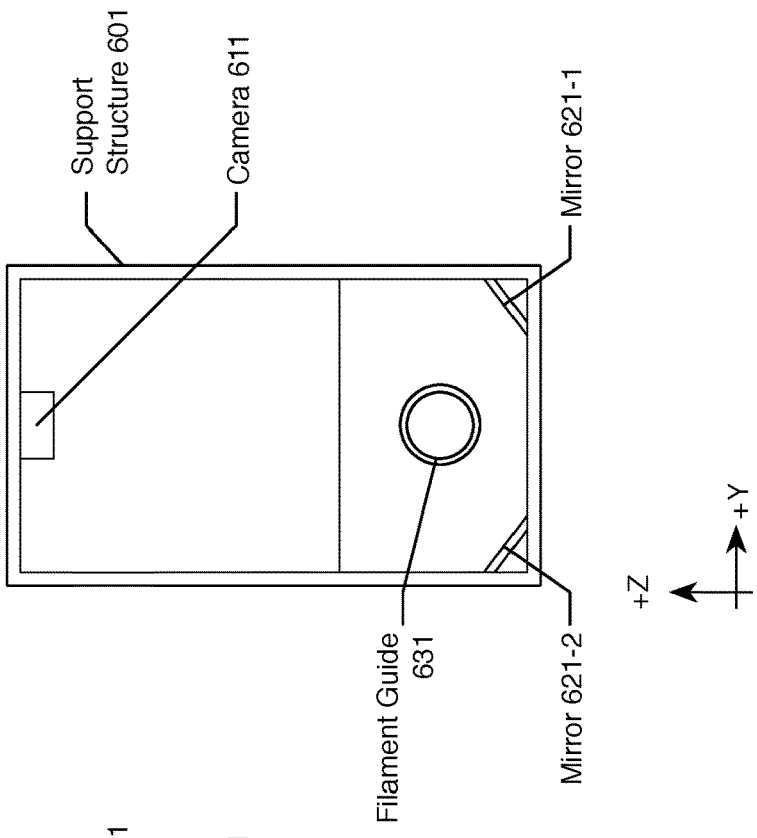
FIG. 6c depicts the side orthographic view of the salient components of single-filament optical sensor 121 in accordance with the illustrative embodiments of the present invention without filament 101.
Figure 6D:
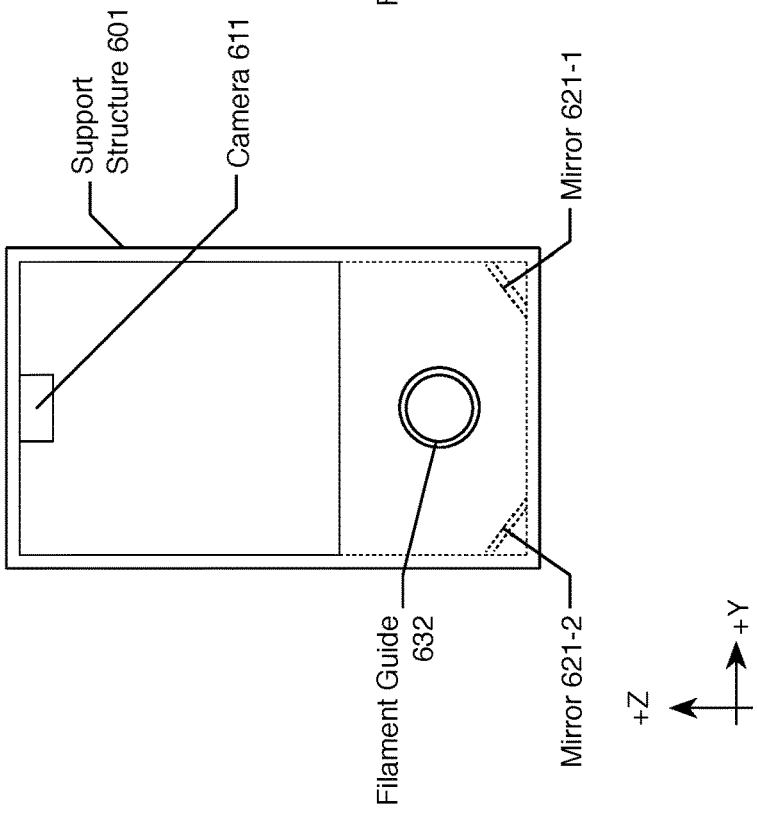
FIG. 6d depict an orthographic side view—along cross-section YY-YY—of single-filament optical sensor 121 without filament 101.

FIGS. 6*a*, 6*b*, and 6*c* depict front, top, and side orthographic views, respectively, of the salient components of single-filament optical sensor 121 in accordance with the illustrative embodiments of the present invention without filament 101. FIG. 6*d* depict an orthographic side view—along cross-section YY-YY—of single-filament optical sensor 121 without filament 101. FIGS. 7*a*, 7*b*, and 7*c* depict front, top, and side orthographic views, respectively, of the salient components of single-filament optical sensor 121 in accordance with the illustrative embodiments of the present invention with filament 101. FIG. 7*d* depict an orthographic side view—along cross-section ZZ-ZZ—of single-filament optical sensor 121 without filament 101.

Single-filament optical sensor 121 comprises: support structure 601, camera 611, mirror 621-1, mirror 621-2, filament guide 631, filament guide 632, filament path 651, and filament 101.

Support structure 601 is made of acrylic, and support structure 601 establishes and maintains the relative spatial position of camera 611, mirror 621-1, mirror 621-2, filament guide 631, filament guide 632, and filament 101, while filament 101 passes through single-filament optical sensor 121. Support structure 601 is made of acrylic so that it does not hinder ambient light from illuminating filament 101. It will be clear to those skilled in the art, after reading this disclosure, how to make and use support structure 601. Furthermore, it will be clear to those skilled in the art, after reading this disclosure, how to make and use a support structure that comprises a different material and/or has different dimensions.

Camera 611 generates a continuous stream of video frames as filament 101 moves through single-filament optical sensor 121. In accordance with the illustrative embodiment, each video stream simultaneously embodies three different images of filament 101, such that each image depicts the same segment comprises three different images in which each image is of a different radial profile of a segment or cross-section of filament 101 from a different radial perspective. For example, FIG. 8 depicts one video frame from camera 611, which video frame comprises filament image 101—90°, filament image 101—210°, and filament image 101-330*g*. Referring to FIG. 6*d*, camera 611 captures filament image 101—90° directly; camera 611 captures filament image 101—210° indirectly by reflection off of mirror 621-2, and camera 611 captures filament image 101—330° indirectly by reflection off of mirror 621-1.

In FIG. 8, the radial profiles in filament image 101—210° and filament image 101—330° appear to be narrower that radial profile in filament image 101—90°. This is because mirrors 621-1 and 621-2 make the radial profiles in filament image 101—210° and filament image 101—330° appear to be farther from camera 611 than the direct-path image. It will be clear to those skilled in the art, after reading this disclosure, how to normalize the widths of filament image 101—210° and 101-330°. It will be clear to those skilled in the art how to make and use camera 611.

Mirror 621-1 is a planar mirror whose reflective surface lies in a first plane that is parallel with the longitudinal axis of filament path 651 and the longitudinal axis of filament 101. Mirror 621-1 is positioned at an angle that reflects the image of filament 101 from a 330° radial perspective into camera 611. It will be clear to those skilled in the art how to determine that angle. Similarly, mirror 621-2 is a planar mirror whose reflective surface lies in a second plane that is parallel with the longitudinal axis of filament path 651 and the longitudinal axis of filament 101. Mirror 621-2 is positioned at an angle that reflects the image of filament 101 from a 210° radial perspective into camera 611. It will be clear to those skilled in the art how to determine that angle. Furthermore, the plane that contains the reflective of surface mirror 621-1 is not parallel to the plane that contains the reflective of surface mirror 621-2.

Filament path 651 is not a tangible structure but is a region of space between filament guide 631 and filament guide 632 into which filament guide 631 and filament guide 632 position and maintain filament 101 while it is moving through single-filament optical sensor 121. In accordance with the illustrative embodiment, filament path 651 occupies the same volume—and has the same shape—as filament 101, and filament path 651 comprises a longitudinal axis that is coexistent with the longitudinal axis of filament 101.

Filament guide 631 and filament guide 632 each comprise a ring of low-friction micro roller bearings that are capable of reliably positioning filament 101 in filament path 651, which ensures that filament 101 maintains approximately the same spatial position with respect to camera 611 and mirrors 621-1 and 621-2 while it moves through single-filament optical sensor 121. It will be clear to those skilled in the art how to make and use filament guides 631 and 632.

Figure 9:
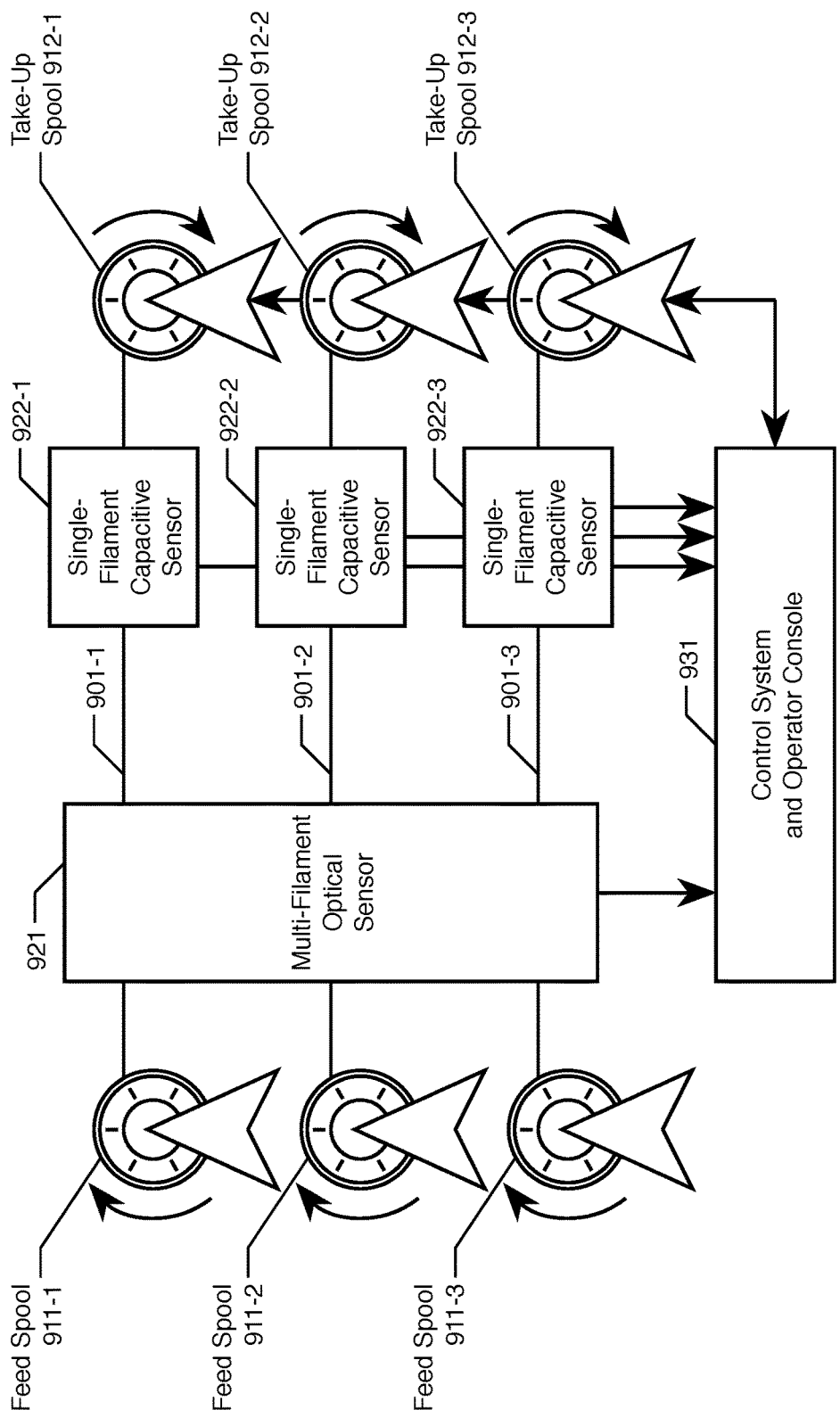
FIG. 9 depicts a schematic diagram of the salient components of multi-filament inspection system 900.

FIG. 9 depicts a schematic diagram of the salient components of multi-filament inspection system 900. System 900 comprises:
(i) three filaments: filament 901-1, filament 901-2, and filament 901-3;
(ii) three feed spools: feed spool 911-1, feed spool 911-2, and feed spool 911-3;
(iii) three take-up spools: spool 912-1, spool 912-2, and spool 912-3;
(iv) multi-filament optical sensor 921;
(v) three single-filament capacitive sensors: single-filament capacitive sensor 922-1, single-filament capacitive sensor 922-2, and single-filament capacitive sensor 922-3; and
(vi) control system and operator console 131.

In accordance with the illustrative embodiment, the following three operations are performed independently and concurrently:
(i) filament 901-1 is unspooled from feed spool 911-1, fed through path 971-1 in multi-filament optical sensor 921 and single-filament capacitive sensor 922-1, and re-spooled onto take-up spool 912-1, all under the direction and supervision of control system and operator console 931; and
(ii) filament 901-2 is unspooled from feed spool 911-2, fed through path 971-2 in multi-filament optical sensor 921 and single-filament capacitive sensor 922-2, and re-spooled onto take-up spool 912-2, all under the direction and supervision of control system and operator console 931; and
(iii) filament 901-3 is unspooled from feed spool 911-3, fed through path 971-3 in multi-filament optical sensor 921 and single-filament capacitive sensor 922-3, and re-spooled onto take-up spool 912-3, all under the direction and supervision of control system and operator console 931.

Filament 901-1, filament 901-2, and filament 901-3 are each identical to filament 101 described above and in the accompanying figures.

Take-up spool 912-1, take-up spool 912-2, and take-up spool 912-3 are each identical to take-up spool 112 described above and in the accompanying figures. In accordance with the illustrative embodiment, the capacity and winding speed of each of take-up spool 912-1, take-up spool 912-2, and take-up spool 912-3 can be the same or different. Furthermore, control system and operator console 931 can wind each of take-up spool 912-1, take-up spool 912-2, and take-up spool 912-3 synchronously or independently.

Feed spool 911-1, feed spool 911-2, and feed spool 911-3 are each identical to feed spool 111 described above and in the accompanying figures. In accordance with the illustrative embodiment, the capacity and filament tension created by each of feed spool 911-1, feed spool 911-2, and feed spool 911-3 can be the same or different.

Figure 12:
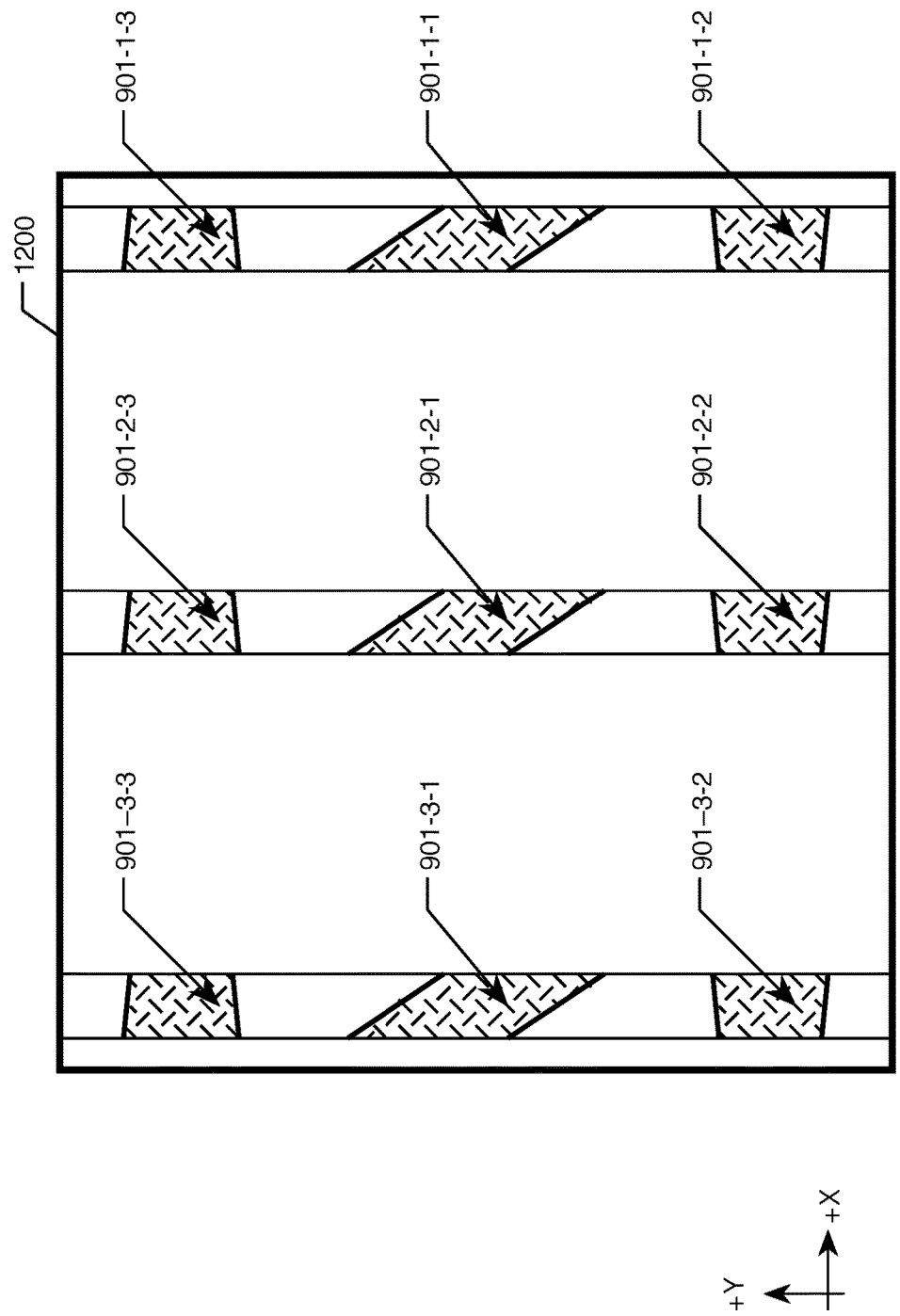
FIG. 12 depicts one frame of the video feed from multi-filament optical sensor 921, which frame comprises filament image 901-1-1, filament image 901-1-2, and filament image 901-1-3 (of filament 901-1), filament image 901-2-1, filament image 901-2-2, and filament image 901-2-3 (of filament 901-2), and filament image 901-3-1, filament image 901-3-2, and filament image 901-3-3 (of filament 901-3).

Multi-filament optical sensor 921 comprises a digital video camera that generates a high-resolution video signal in which each video frame (as shown in FIG. 12) embodies three different images of filament 901-1, three different images of filament 901-2, and three different images of filament 901-3, for a total of nine images. In particular, each frame comprises filament image 901-1-1, filament image 901-1-2, and filament image 901-1-3 (of filament 901-1), filament image 901-2-1, filament image 901-2-2, and filament image 901-2-3 (of filament 901-2), and filament image 901-3-1, filament image 901-3-2, and filament image 901-3-3 (of filament 901-3). Each of the three images of each filament is taken from a different perspective around the filament. For example, one image—image 901-1-1—is taken from one perspective; one image—image 901-2-2—is taken from a second perspective, and one image—image 901-3-3—is taken from a third perspective. The video signal from multi-filament optical sensor 121 is provided, in well-known fashion, to control system and operator console 931 for analysis and processing. Multi-filament optical sensor 921 is described in detail below and in the accompanying figures.

Single-filament capacitive sensor 922-1, single-filament capacitive sensor 922-2, and single-filament capacitive sensor 922-3 are each identical to single-filament capacitive sensor 122 described above and in the accompanying figures. The measure of the permittivity generated by single-filament capacitive sensor 922-1, single-filament capacitive sensor 922-2, and single-filament capacitive sensor 922-3 are each continuously provided, in well-known fashion, to control system and operator console 931 for analysis and processing.

Control system and operator console 931 comprises hardware and software to:
(i) control the unspooling and spooling of filament 901-1, filament 901-2, and filament 901-3, and
(ii) receive, process, and interpret the images of the various radial profiles in the stream of video frames from multi-filament optical sensor 921, and
(iii) receive, process, and interpret the permittivity measurements from single-filament capacitive sensor 922-1, single-filament capacitive sensor 922-2, and single-filament capacitive sensor 922-3, and
(iv) interact with a human operator (who is not shown in FIG. 9), and
(v) determine the physical properties of each segment of filament 901-1, filament 901-2, and filament 901-3, and
(vi) determine whether the physical and chemical properties of each segment of filament 901-1, filament 901-2, and filament 901-3 are within specification tolerance, and
(vii) to associate each position along the 3000 meters of filament 901-1, filament 901-2, and filament 901-3 with those physical properties.

It will be clear to those skilled in the art, after reading this disclosure, how to make and use control system and operator console 131.

Figure 10A:
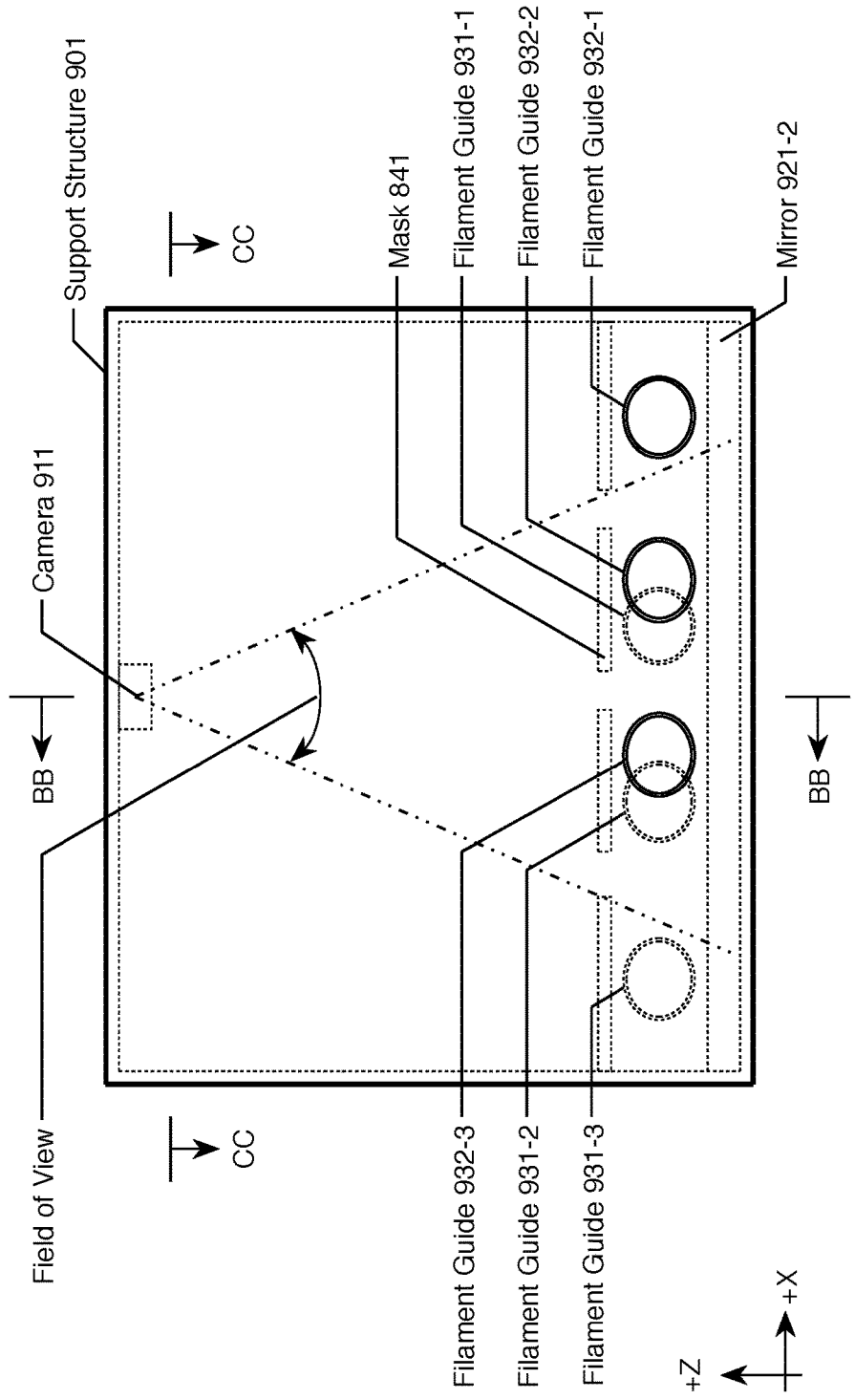
FIG. 10a depicts the orthographic front view of multi-filament optical sensor 921 without any filaments.
Figure 10B:
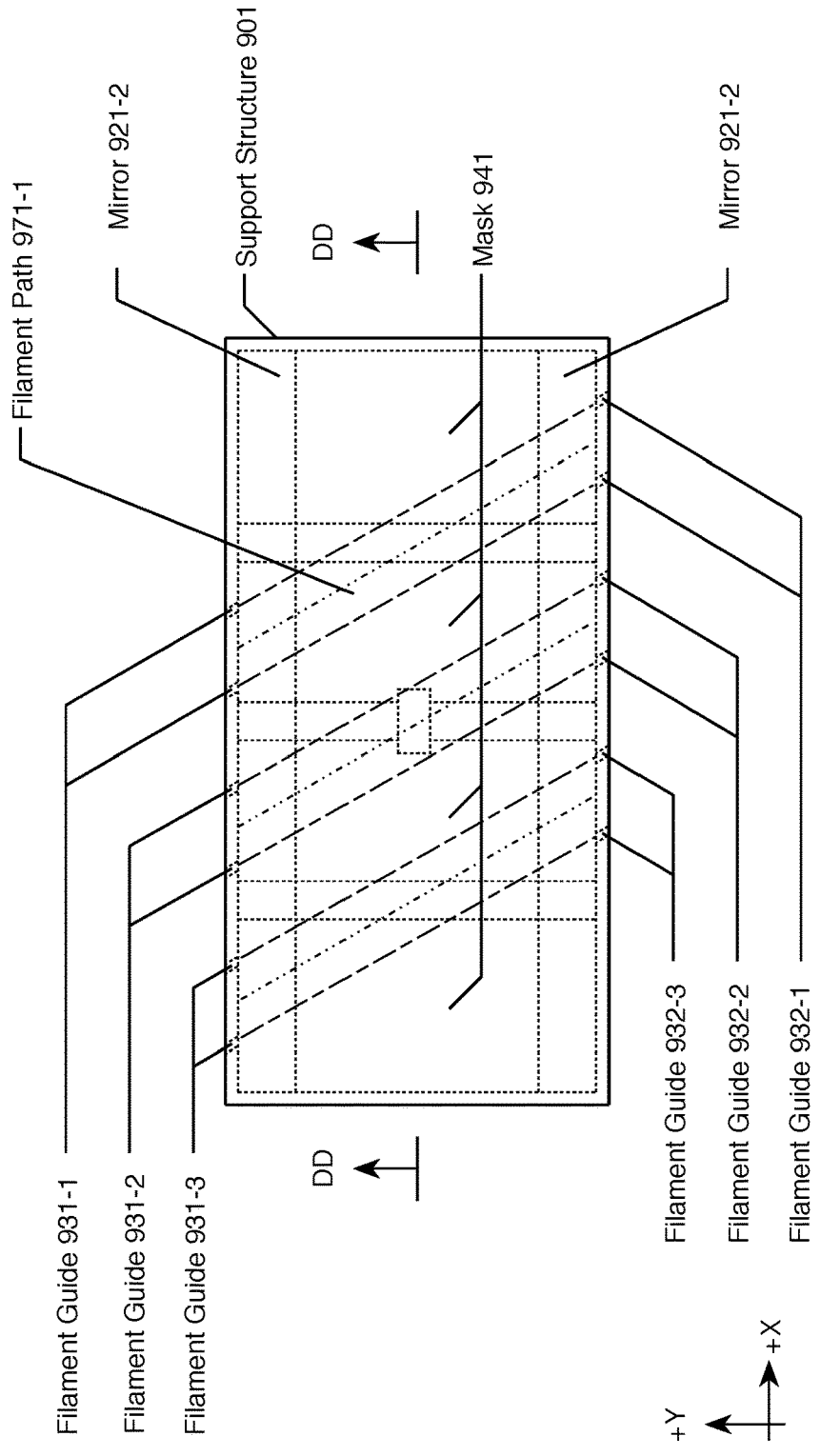
FIG. 10b depicts the orthographic top view of multi-filament optical sensor 921 without any filaments.
Figure 10C:
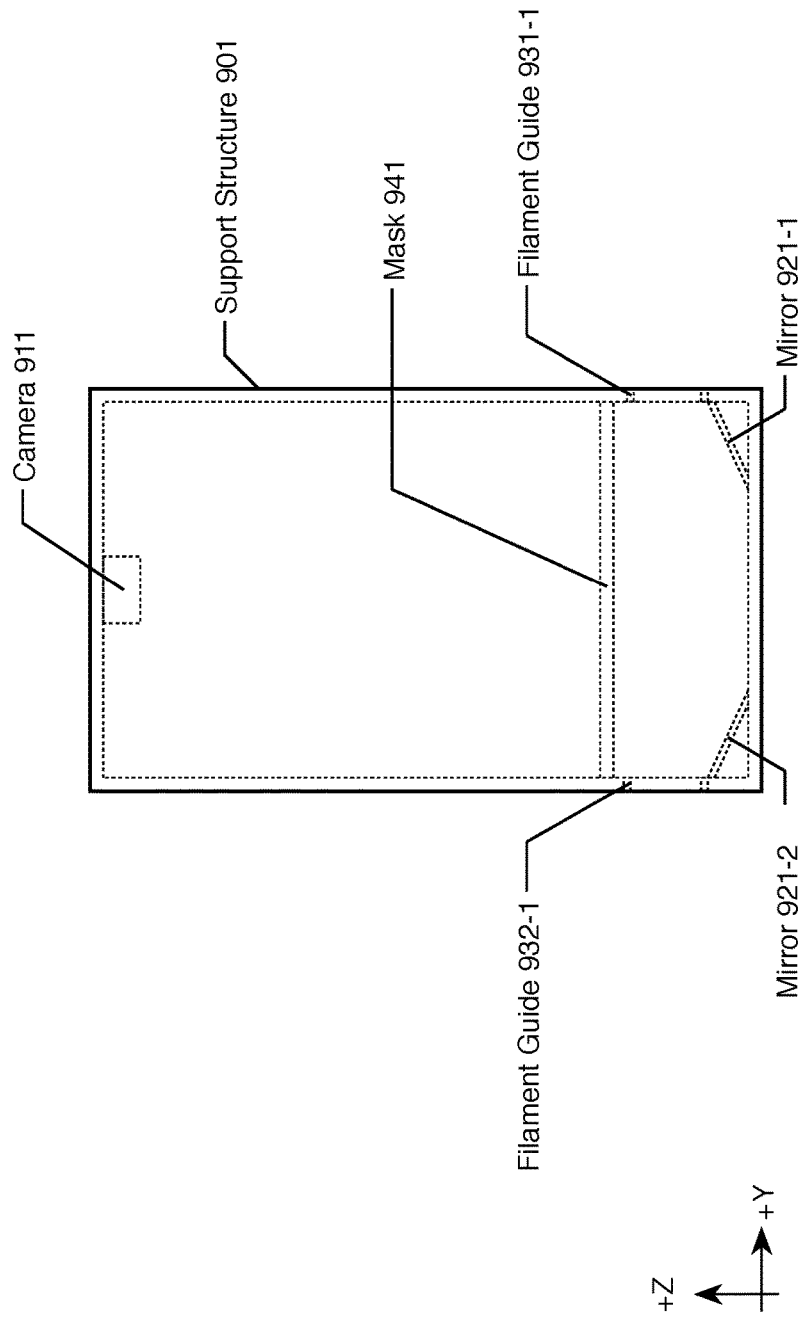
FIG. 10c depicts the orthographic side view of multi-filament optical sensor 921 without any filaments.
Figure 10D:
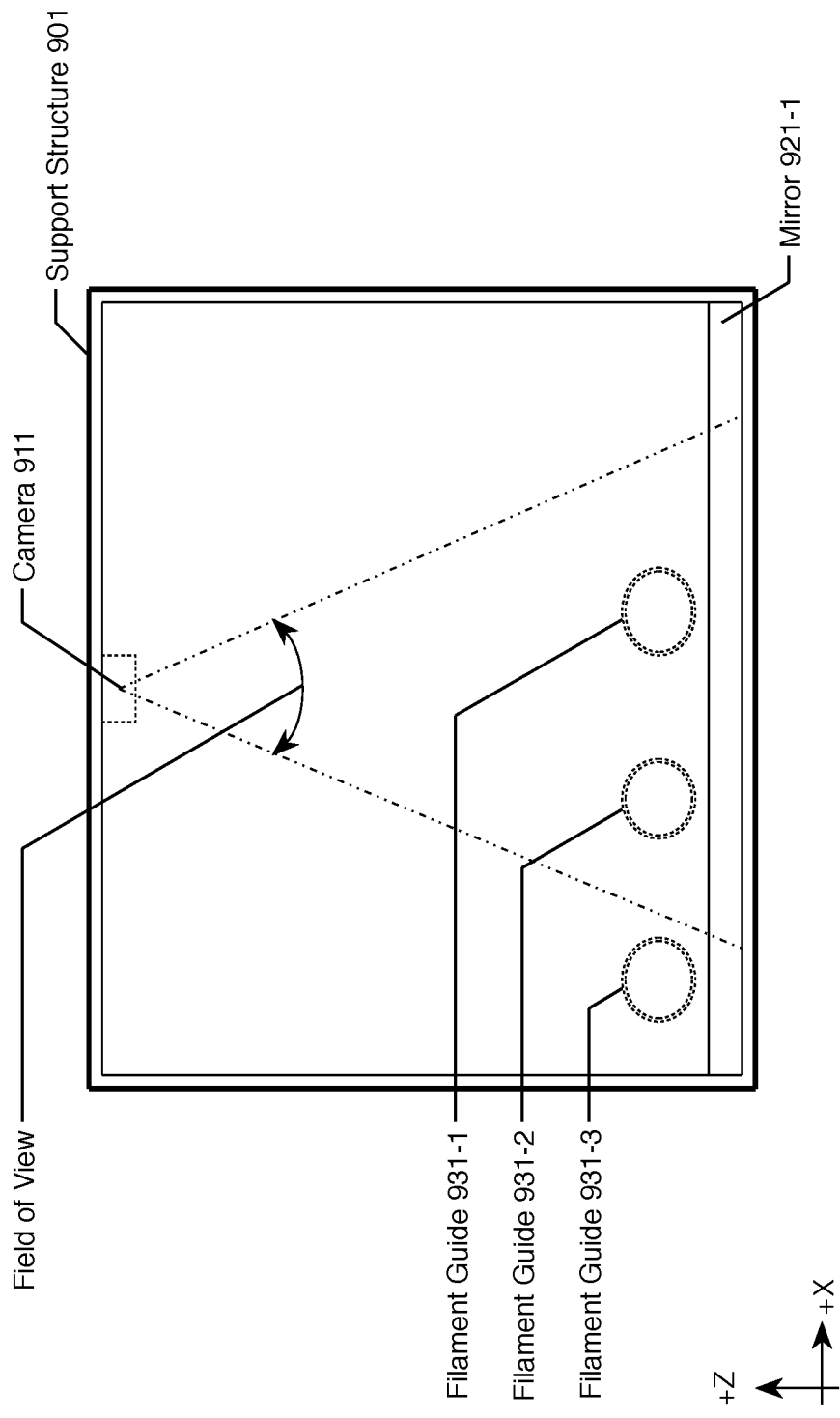
FIG. 10d depicts an orthographic front view along cross-section DD-DD multi-filament optical sensor 921 without any filaments.
Figure 10E:
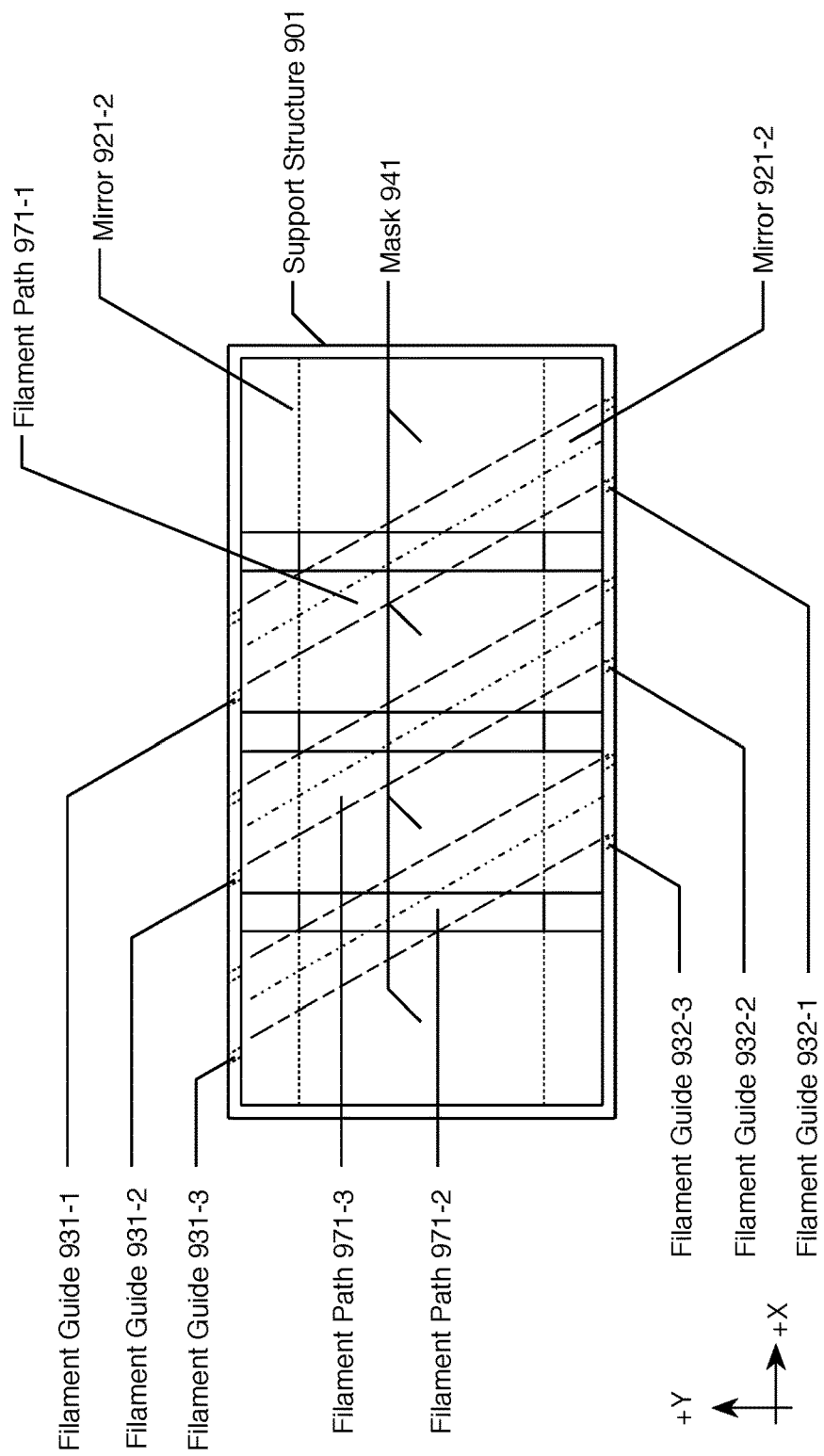
FIG. 10e depicts an orthographic top view along cross-section CC-CC multi-filament optical sensor 921 without any filaments.
Figure 10F:
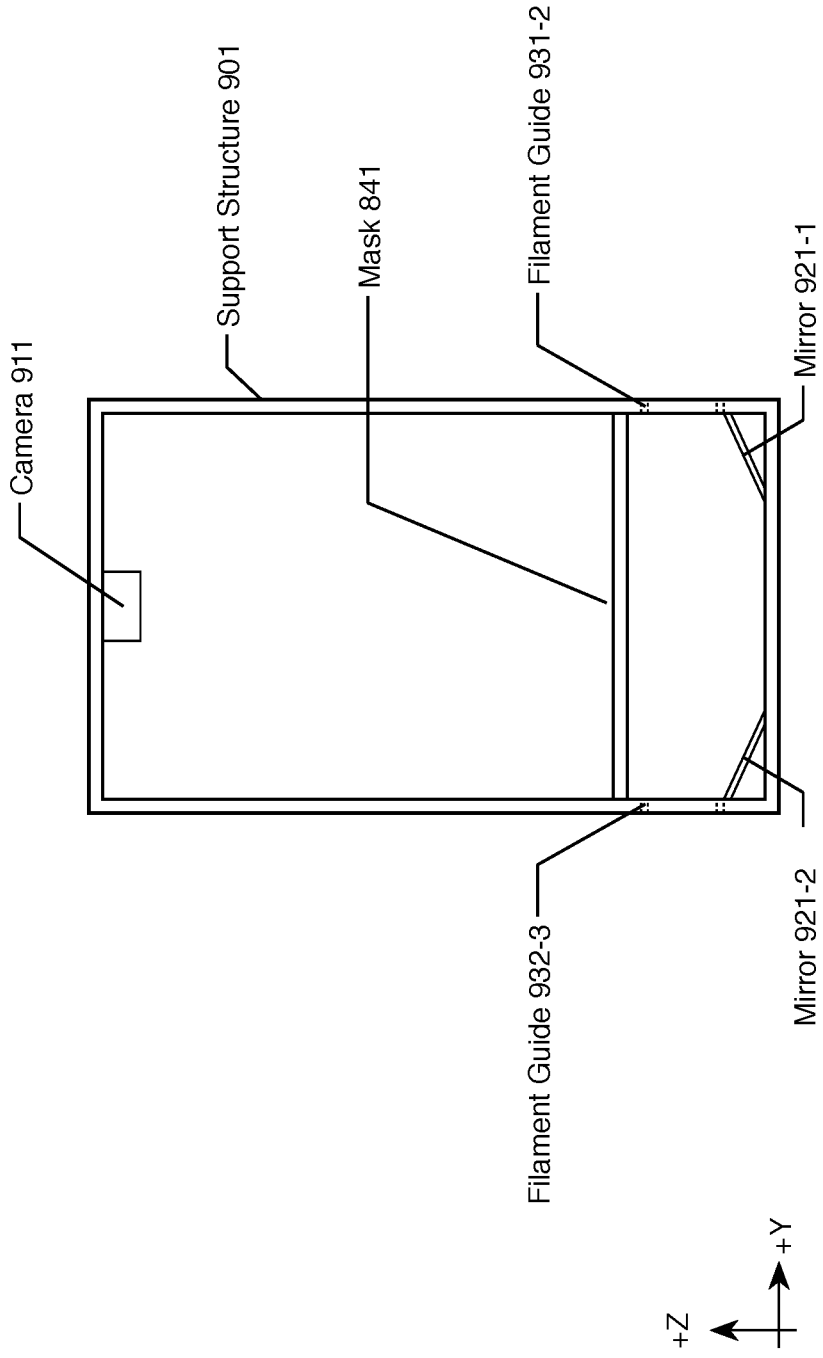
FIG. 10f depicts an orthographic side view along cross-section BB-BB multi-filament optical sensor 921 without any filaments.

FIGS. 10a, 10b, 10c depict orthographic front, top, and side views, respectively, of multi-filament optical sensor 921 without any filaments. FIG. 10d depicts an orthographic front view along cross-section DD-DD multi-filament optical sensor 921 without any filaments. FIG. 10e depicts an orthographic top view along cross-section CC-CC multi-filament optical sensor 921 without any filaments. FIG. 10f depicts an orthographic side view along cross-section BB-BB multi-filament optical sensor 921 without any filaments.

Figure 11A:
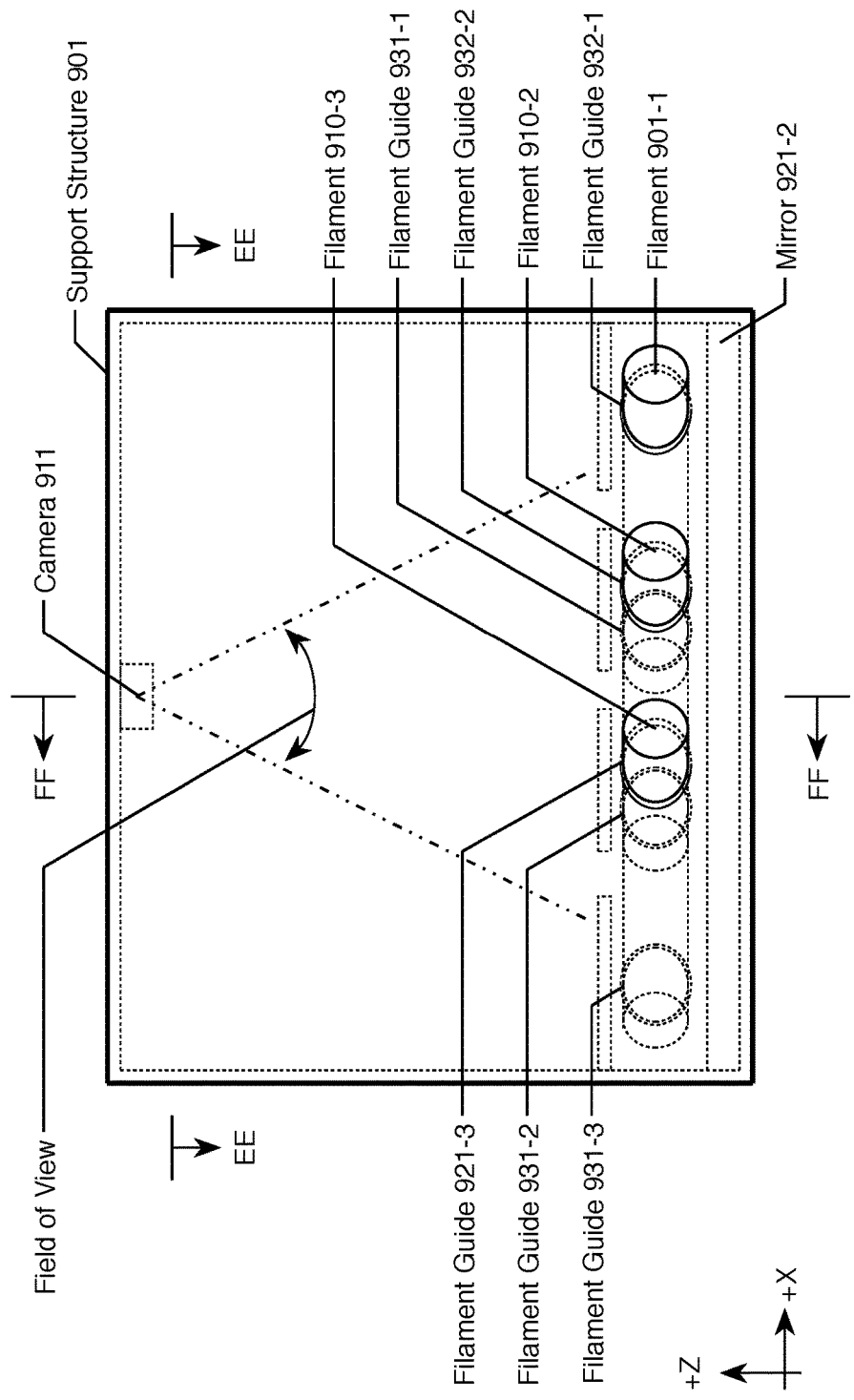
FIG. 11a depicts the orthographic front view of multi-filament optical sensor 921 with filament 901-1, filament 901-2, and filament 901-3.
Figure 11B:
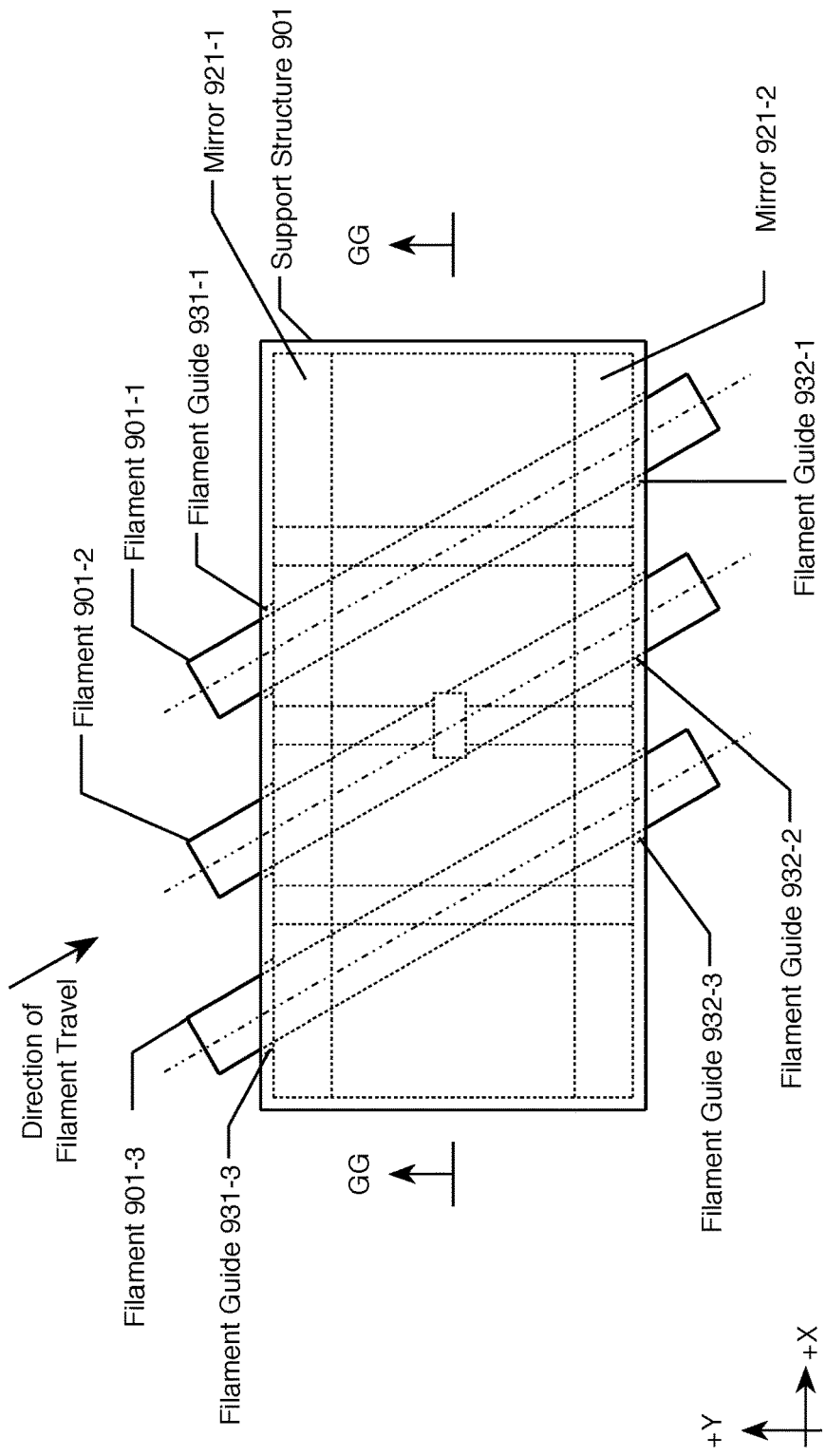
FIG. 11b depicts the orthographic top view of multi-filament optical sensor 921 with filament 901-1, filament 901-2, and filament 901-3.
Figure 11C:
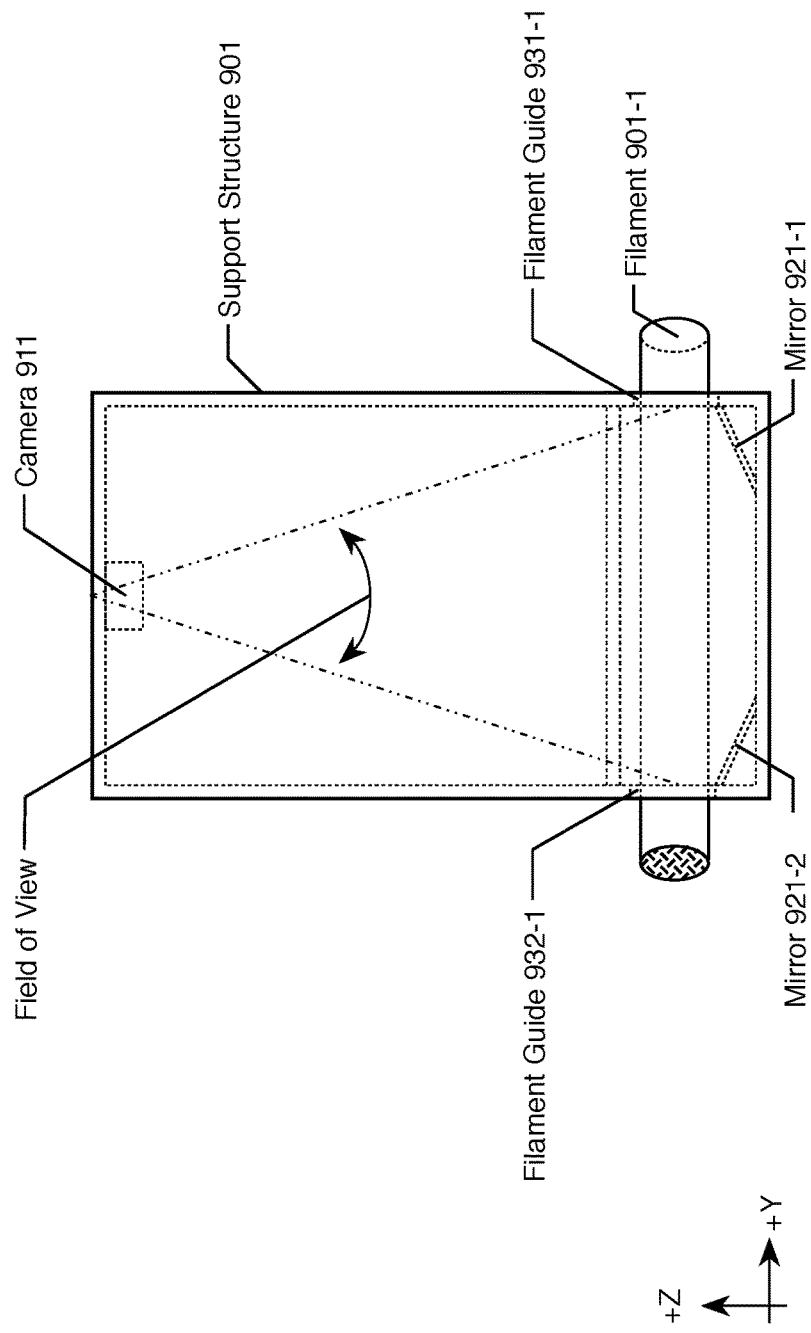
FIG. 11c depicts the orthographic side view of multi-filament optical sensor 921 with filament 901-1, filament 901-2, and filament 901-3.
Figure 11D:
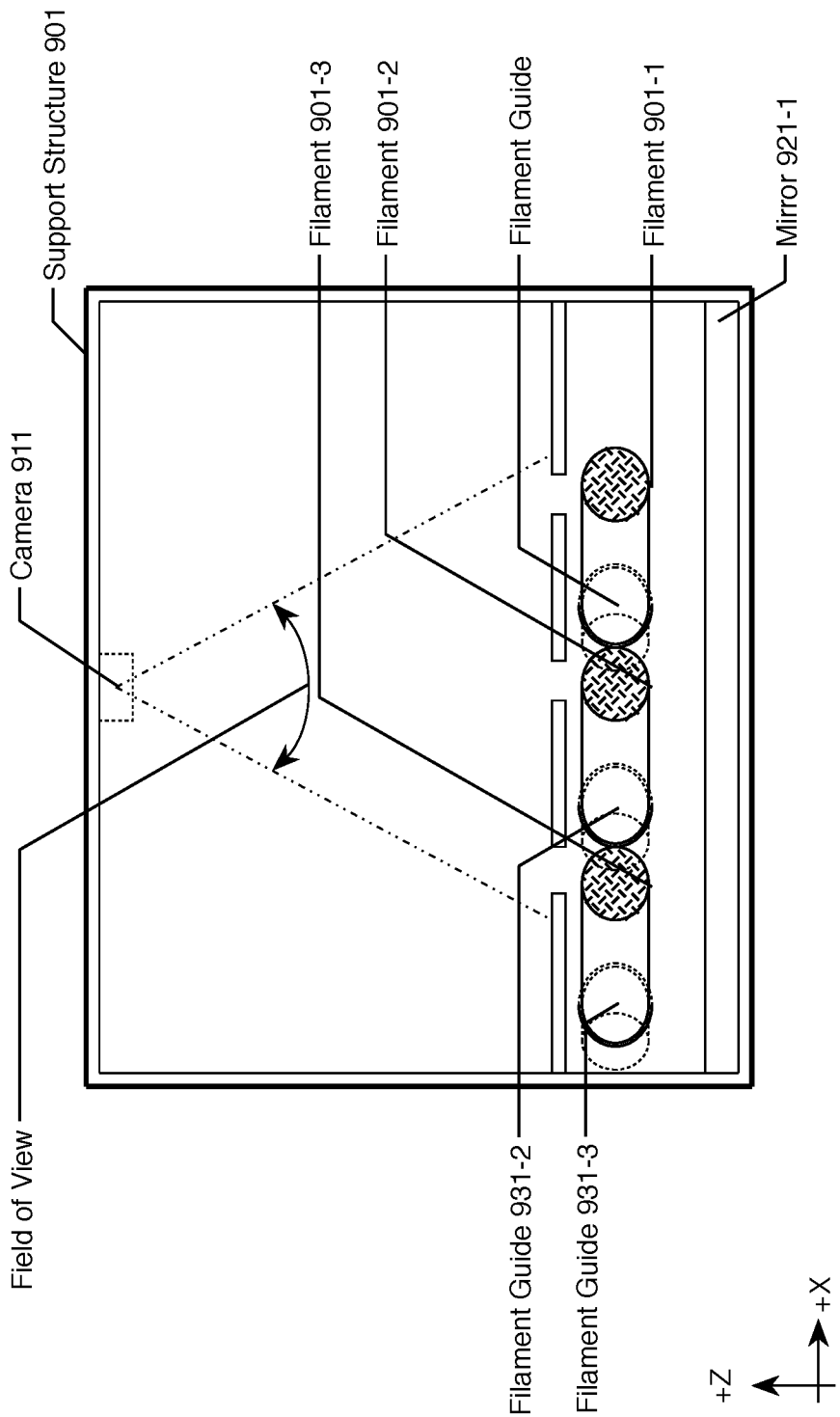
FIG. 11d depicts an orthographic front view along cross-section GG-GG multi-filament optical sensor 921 with filament 901-1, filament 901-2, and filament 901-3.
Figure 11E:
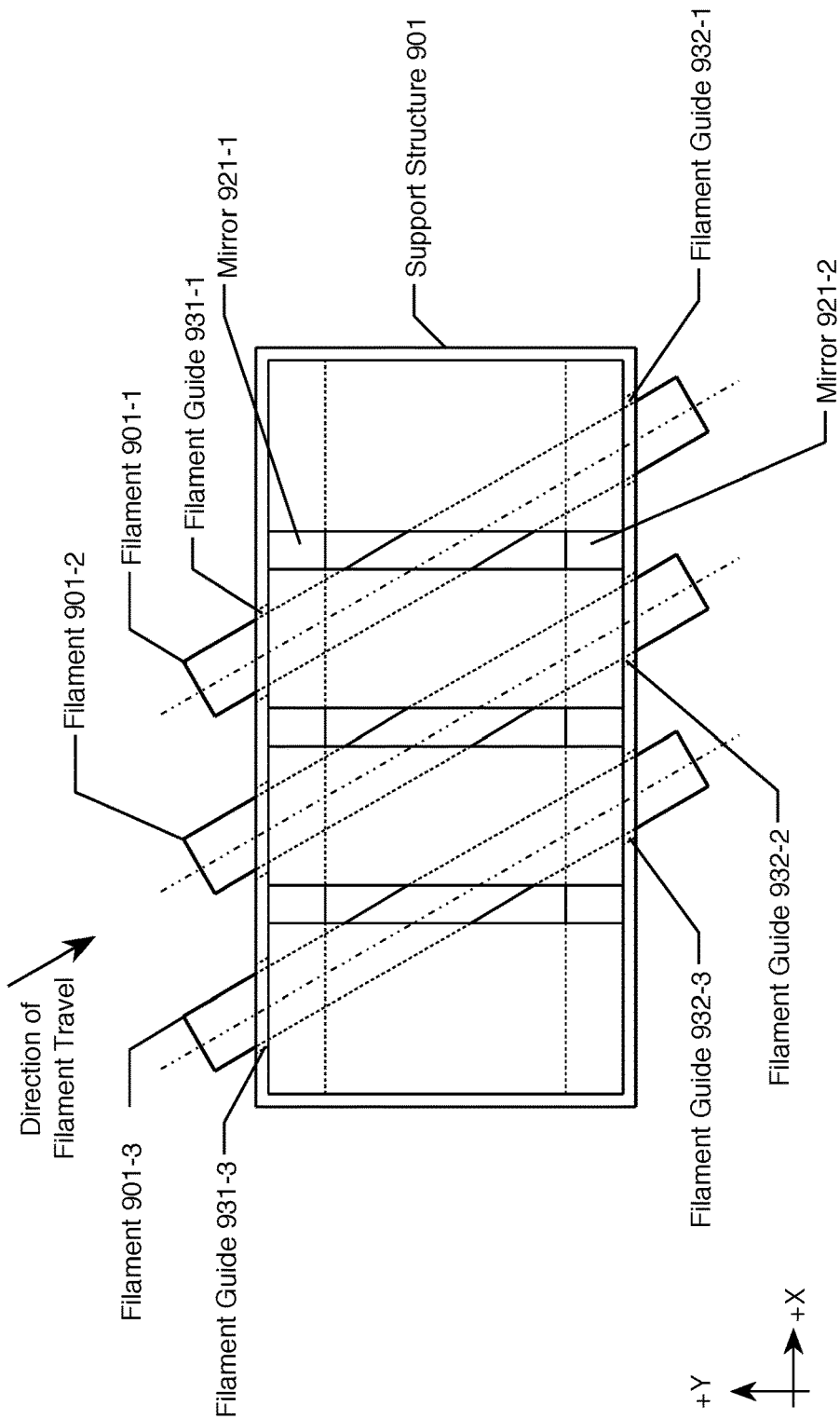
FIG. 11e depicts an orthographic top view along cross-section EE-EE multi-filament optical sensor 921 with filament 901-1, filament 901-2, and filament 901-3.
Figure 11F:
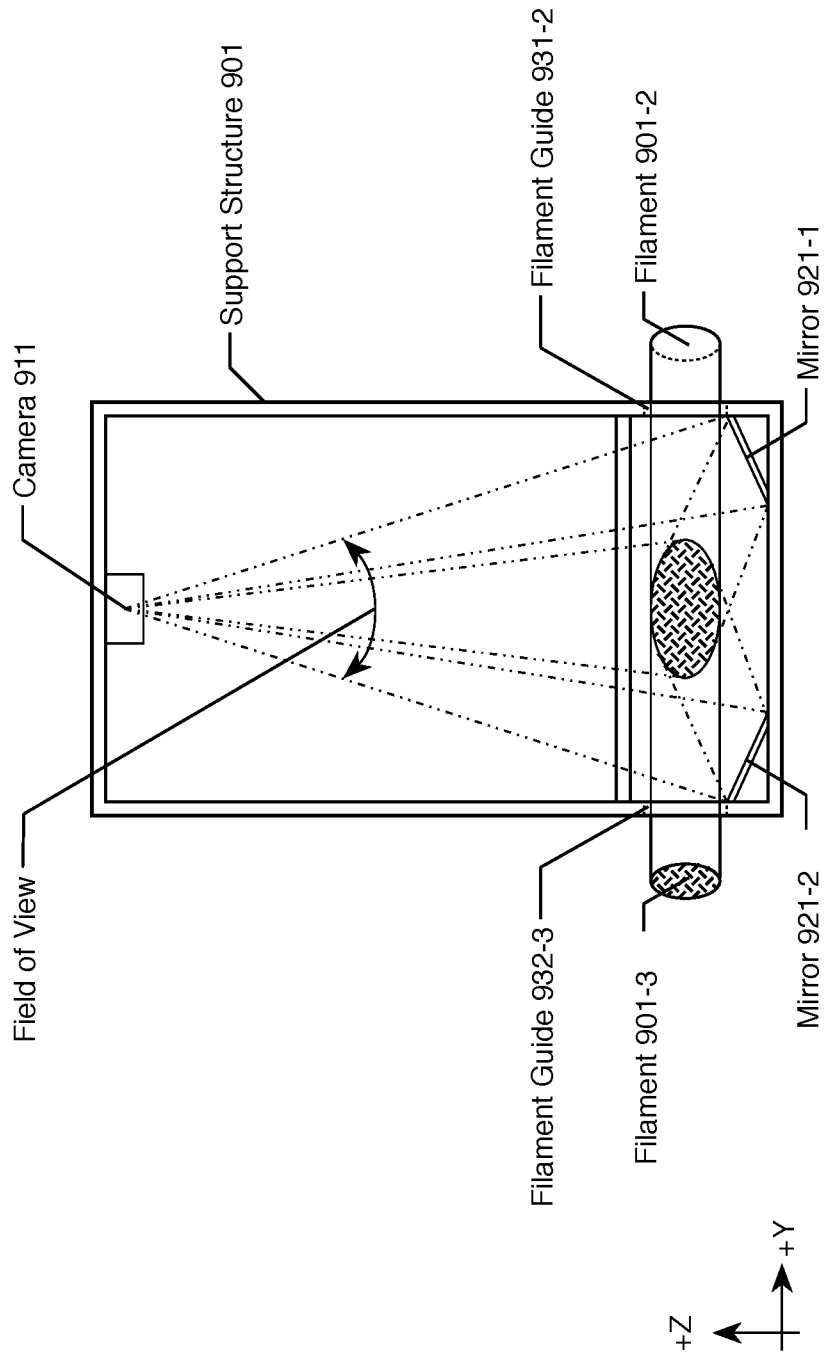
FIG. 11f depicts an orthographic side view along cross-section FF-FF multi-filament optical sensor 921 with filament 901-1, filament 901-2, and filament 901-3.

FIGS. 11a, 11b, 11c depict orthographic front, top, and side views, respectively, of multi-filament optical sensor 921 with filament 901-1, filament 901-2, and filament 901-3. FIG. 11d depicts an orthographic front view along cross-section GG-GG multi-filament optical sensor 921 with filament 901-1, filament 901-2, and filament 901-3. FIG. 11e depicts an orthographic top view along cross-section EE-EE multi-filament optical sensor 921 with filament 901-1, filament 901-2, and filament 901-3. FIG. 11f depicts an orthographic side view along cross-section FF-FF multi-filament optical sensor 921 with filament 901-1, filament 901-2, and filament 901-3.

Multi-filament optical sensor 921 comprises: support structure 901, camera 911, mirror 921-1, mirror 921-2, filament guide 931-1, filament guide 931-2, filament guide 931-3, filament guide 932-1, filament guide 932-2, filament guide 932-3, filament path 971-1, filament path 971-2, filament path 971-3, filament 901-1, filament 901-2, and filament 901-3, interrelated as shown.

Support structure 901 is made of acrylic, and support structure 901 establishes and maintains the relative spatial position of camera 911, mirror 921-1, mirror 921-2, filament guide 931-1, filament guide 931-2, filament guide 931-3, filament guide 932-1, filament guide 932-2, filament guide 932-3, filament 901-1, filament 901-2, and filament 901-3, while filament 901-1, filament 901-2, and filament 901-3 passes through multi-filament optical sensor 921. Support structure 901 is made of acrylic so that it does not hinder ambient light from illuminating filament 901-1, filament 901-2, and filament 901-3. It will be clear to those skilled in the art, after reading this disclosure, how to make and use support structure 901. Furthermore, it will be clear to those skilled in the art, after reading this disclosure, how to make and use a support structure that comprises a different material and/or has different dimensions.

Camera 911 generates a continuous stream of video frames as filament 901-1, filament 901-2, and filament 901-3 move through single-filament optical sensor 121. In accordance with the illustrative embodiment, each video stream simultaneously embodies three different images of filament 901-1, three different images of filament 901-2, and three different images of filament 901-3, for a total of nine images. In particular, each frame comprises filament image 901-1-1, filament image 901-1-2, and filament image 901-1-3 (of filament 901-1), filament image 901-2-1, filament image 901-2-2, and filament image 901-2-3 (of filament 901-2), and filament image 901-3-1, filament image 901-3-2, and filament image 901-3-3 (of filament 901-3).

Each of the three images of each filament is taken from a different perspective, and yet all three images compose all of the exterior boundary of an segment of the filament. Referring to FIG. 12, camera 911 captures filament image 901-1-1, filament image 901-2-1, and filament image 901-3-1 directly; camera 911 captures filament image 901-1-2, filament image 901-2-2, and filament image 901-3-2 indirectly by reflection off of mirror 621-2, and camera 911 captures filament image 901-1-3, filament image 901-2-3, and filament image 901-3-3 indirectly by reflection off of mirror 621-1.

In FIG. 12, the respective images are distorted because of the relative angles of the filaments with respect to the reflective surfaces of mirrors 621-1 and 621-2 and camera 911. It will be clear to those skilled in the art, after reading this disclosure, how to normalize the widths of filament images.

Mirror 621-1 is a planar mirror whose reflective surface lies in a first plane such that the first plane and the longitudinal axis of filament 901-2 at a point intersect at a first angle ø1, wherein 0°<ø1<90π. Similarly, mirror 621-2 is a planar mirror whose reflective surface lies in a second plane such that the second plane and the longitudinal axis of filament 901-2 at a second point intersect at a second angle ø2, wherein 0°<ø2<90°.

Filament path 971-1 is not a tangible structure but is a region of space between filament guide 931-1 and filament guide 932-1 into filament 901-1 is positioned and maintained while it is moving through multi-filament optical sensor 921. In accordance with the illustrative embodiment, filament path 971-1 occupies the same volume—and has the same shape—as filament 901-1, and filament path 971-1 comprises a longitudinal axis that is coexistent with the longitudinal axis of filament 901-1.

Filament guide 931-1 and filament guide 932-1 each comprise a ring of low-friction micro roller bearings that are capable of reliably positioning filament 901-1 in filament path 971-1, which ensures that filament 901-1 maintains approximately the same spatial position with respect to camera 911 and mirrors 921-1 and 921-2 while it moves through multi-filament optical sensor 921. It will be clear to those skilled in the art how to make and use filament guides 931-1 and 932-1.

Filament path 971-2 is not a tangible structure but is a region of space between filament guide 931-2 and filament guide 932-2 into filament 901-2 is positioned and maintained while it is moving through multi-filament optical sensor 921. In accordance with the illustrative embodiment, filament path 971-2 occupies the same volume—and has the same shape—as filament 901-2, and filament path 971-2 comprises a longitudinal axis that is coexistent with the longitudinal axis of filament 901-2.

Filament guide 931-2 and filament guide 932-2 each comprise a ring of low-friction micro roller bearings that are capable of reliably positioning filament 901-2 in filament path 971-2, which ensures that filament 901-2 maintains approximately the same spatial position with respect to camera 911 and mirrors 921-2 and 921-2 while it moves through multi-filament optical sensor 921. It will be clear to those skilled in the art how to make and use filament guides 931-2 and 932-2.

Filament path 971-3 is not a tangible structure but is a region of space between filament guide 931-3 and filament guide 932-3 into filament 901-3 is positioned and maintained while it is moving through multi-filament optical sensor 921. In accordance with the illustrative embodiment, filament path 971-3 occupies the same volume—and has the same shape—as filament 901-3, and filament path 971-3 comprises a longitudinal axis that is coexistent with the longitudinal axis of filament 901-3.

Filament guide 931-3 and filament guide 932-3 each comprise a ring of low-friction micro roller bearings that are capable of reliably positioning filament 901-3 in filament path 971-3, which ensures that filament 901-3 maintains approximately the same spatial position with respect to camera 911 and mirrors 921-3 and 921-3 while it moves through multi-filament optical sensor 921. It will be clear to those skilled in the art how to make and use filament guides 931-3 and 932-3.

What is claimed is:

1. A system comprising:
   a first mirror;
   a second mirror;
   a first filament guide and a second filament guide capable of positioning a filament in a path, wherein the path comprises a longitudinal axis at a point;
   a camera capable of generating a video frame that comprises:
   (1) a first image of a first radial profile of a segment of the filament in the path from a first radial perspective, and
   (2) a second image of a second radial profile of the segment of the filament in the path from a second radial perspective, wherein the second image is received by the camera via reflection in the first mirror, and
   (3) a third image of a third radial profile of the segment of the filament in the path from a third radial perspective, wherein the third image is reflected into the camera by the second mirror; and
   an electrical RC circuit for measuring the permittivity of the segment of the filament;
   and
   a support structure for establishing and maintaining the relative spatial relationship of the first mirror, the second mirror, the first filament guide, the second filament guide, and the camera.

2. The system of claim 1:
   wherein the first mirror is planar and lies in a first plane;
   wherein the second mirror is planar and lies in a second plane;
   wherein the first plane and the longitudinal axis at the point are parallel;
   wherein the second plane and the longitudinal axis at the point are parallel; and
   wherein the first plane and the second plane are not parallel.

3. The system of claim 1 wherein a first angle between the first radial perspective and the second radial perspective is 120°; and
   wherein a second angle between the first radial perspective and the third radial perspective is 120°.

4. The system of claim 1 wherein at least one of the first image, the second image, and the third image composes all of the exterior boundary of the segment of the filament.

5. A system comprising:
   a first mirror;
   a second mirror;
   a first filament guide and a second filament guide capable of positioning a first filament in a first path, wherein the first path comprises a first longitudinal axis at a first point;
   a third filament guide and a fourth filament guide capable of positioning a second filament in a second path, wherein the second path comprises a second longitudinal axis at a second point;
   a camera capable of generating a video frame that comprises:
   (1) a first image of a first radial profile of a first segment of the first filament in the first path from a first perspective, and
   (2) a second image of a second radial profile of the first segment of the first filament in the first path from a second perspective, wherein the second image is received by the camera via reflection in the first mirror, and
   (3) a third image of a third radial profile of the first segment of the first filament in the first path from a third perspective, wherein the third image is received by the camera via reflection in the second mirror, and
   (4) a fourth image of a fourth radial profile of a second segment of the second filament in the second path from a fourth perspective, and
   (5) a fifth image of a fifth radial profile of the second segment of the second filament in the second path from a fifth perspective, wherein the fifth image is received by the camera via reflection in the first mirror, and
   (6) a sixth image of a sixth radial profile of the second segment of the second filament in the second path from a sixth perspective, wherein the sixth image is received by the camera via reflection in the second mirror; and
   a support structure for establishing and maintaining the relative spatial relationship of the first mirror, the second mirror, the first filament guide, the second filament guide, the third filament guide, the fourth filament guide, and the camera.

6. The system of claim 5:
   wherein the first mirror is planar and lies in a first plane;
   wherein the second mirror is planar and lies in a second plane;
   wherein the first plane and the first longitudinal axis at the first point intersect at a first angle ø1, wherein 0°<ø1<90°;
   wherein the second plane and the first longitudinal axis at the second point intersect at a second angle ø2, wherein 0°<ø2<90°; and
   wherein the first plane and the second plane are not parallel.

7. The system of claim 5 wherein the first longitudinal axis at the first point and the second longitudinal axis at the second point are parallel.

8. The system of claim 5 further comprising an electrical resistor-capacitor circuit for measuring the permittivity of the segment of the filament.

9. The system of claim 5 wherein at least one of the first image, the second image, and the third image composes all of the exterior boundary of the first segment of the first filament.

10. A system comprising:
    a first mirror;
    a second mirror;
    a filament that comprises (i) a longitudinal axis at a point, and (ii) a cross-section at the point; and
    a camera for generating a video frame that comprises:
    (1) a first image of a first radial profile of the cross-section of the filament from a first radial perspective, and
    (2) a second image of a second radial profile of the cross-section of the filament from a second radial perspective, wherein the second image is received by the camera via reflection in the first mirror, and
    (3) a third image of a third radial profile of the cross-section of the filament from a third radial perspective, wherein the third image is reflected into the camera by the second mirror; and an electrical resistor-capacitor circuit for measuring the permittivity of the segment of the filament.

11. The system of claim 10:
wherein the first mirror is planar and lies in a first plane;
wherein the second mirror is planar and lies in a second plane;
wherein the first plane and the longitudinal axis at the point are parallel;
wherein the second plane and the longitudinal axis at the point are parallel; and
wherein the first plane and the second plane are not parallel.

12. The system of claim 10 wherein a first angle between the first radial perspective and the second radial perspective is 120°; and
wherein a second angle between the first radial perspective and the third radial perspective is 120°.

13. The system of claim 10 wherein at least one of the first image, the second image, and the third image composes all of the exterior boundary of the first cross-section.

14. A system comprising:
a first mirror;
a second mirror;
a first filament that comprises (i) a first longitudinal axis at a first point, and (ii) a first cross-section at the first point;
a second filament that comprises (i) a second longitudinal axis at a second point, and (ii) a second cross-section at the second point; and
a camera capable of generating a video frame that comprises:
(1) a first image of a first radial profile of the first cross-section of the first filament from a first perspective, and
(2) a second image of a second radial profile of the first cross-section of the first filament from a second perspective, wherein the second image is received by the camera via reflection in the first mirror, and
(3) a third image of a third radial profile of the first cross-section of the first filament from a third perspective, wherein the third image is reflected into the camera by the second mirror, and
(4) a fourth image of a fourth radial profile of the second cross-section of the second filament from a fourth perspective, and
(5) a fifth image of a fifth radial profile of the second cross-section of the second filament from a second perspective, wherein the fifth image is received by the camera via reflection in the first mirror, and
(6) a sixth image of a sixth radial profile of the second cross-section of the second filament from a third perspective, wherein the third image is reflected into the camera by the second mirror.

15. The system of claim 14:
wherein the first mirror is planar and lies in a first plane;
wherein the second mirror is planar and lies in a second plane;
wherein the first plane and the first longitudinal axis at the first point intersect at a first angle ø1, wherein 0°<ø1<90°;
wherein the second plane and the first longitudinal axis at the second point intersect at a second angle ø2, wherein 0°<ø2<90°; and
wherein the first plane and the second plane are not parallel.

16. The system of claim 14 wherein the first longitudinal axis at the first point and the second longitudinal axis at the second point are parallel.

17. The system of claim 14 further comprising an electrical resistor-capacitor circuit for measuring the permittivity of the segment of the filament.

18. The system of claim 14 wherein at least one of the first image, the second image, and the third image composes all of the exterior boundary of the first segment of the first filament.

* * * * *